US011944268B2

(12) United States Patent
Takahashi

(10) Patent No.: US 11,944,268 B2
(45) Date of Patent: Apr. 2, 2024

(54) ENDOSCOPE ADAPTOR, ROBOTIC SURGICAL SYSTEM, METHOD OF ADJUSTING ROTATIONAL POSITION USING ENDOSCOPE ADAPTOR

(71) Applicant: MEDICAROID CORPORATION, Kobe (JP)

(72) Inventor: Kaoru Takahashi, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 48 days.

(21) Appl. No.: 17/206,155

(22) Filed: Mar. 19, 2021

(65) Prior Publication Data

US 2021/0307592 A1 Oct. 7, 2021

(30) Foreign Application Priority Data

Mar. 30, 2020 (JP) ................................. 2020-061213

(51) Int. Cl.
*A61B 1/00* (2006.01)

(52) U.S. Cl.
CPC ...... *A61B 1/00121* (2013.01); *A61B 1/00149* (2013.01)

(58) Field of Classification Search
CPC ............ A61B 1/00121; A61B 1/00147; A61B 1/00149

See application file for complete search history.

(56) References Cited

U.S. PATENT DOCUMENTS

| 5,876,325 | A | * | 3/1999 | Mizuno | ................. | A61B 34/37 600/117 |
| 6,569,084 | B1 | * | 5/2003 | Mizuno | ................ | A61B 1/0051 600/102 |
| 2015/0105620 | A1 | * | 4/2015 | Oginski | ............. | A61B 1/00147 600/112 |
| 2020/0069385 | A1 | | 3/2020 | Ago et al. | | |
| 2020/0305997 | A1 | | 10/2020 | Ago et al. | | |

FOREIGN PATENT DOCUMENTS

| EP | 3616594 A1 | 3/2020 |
| JP | 2020-031767 A | 3/2020 |
| JP | 6821735 B2 | 1/2021 |
| WO | 2019/139941 A1 | 7/2019 |

* cited by examiner

*Primary Examiner* — Aaron B Fairchild
(74) *Attorney, Agent, or Firm* — METROLEX IP LAW GROUP, PLLC

(57) ABSTRACT

An endoscope adaptor according to an embodiment may include a base portion including a transmission mechanism configured to decelerate and transmit rotation of a driven member configured to be driven to rotate by a drive part of a robot arm to an endoscope holder. The transmission mechanism includes a drive transmission shaft that is configured to be rotated by the rotation of the driven member, a first linkage member that is configured to rotate integrally with the drive transmission shaft, and a second linkage member being rotatable with respect to the drive transmission shaft and configured to rotate with first linkage member in a linked manner. The base portion includes a stopper configured to come in contact with the second linkage member to stop rotation of the drive transmission shaft.

16 Claims, 10 Drawing Sheets

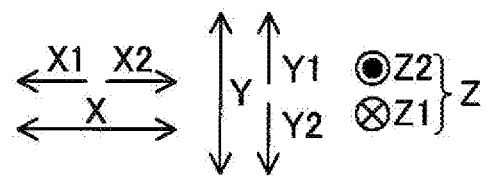
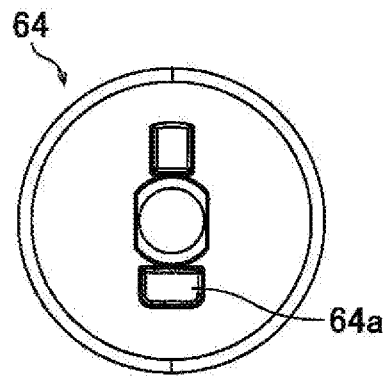
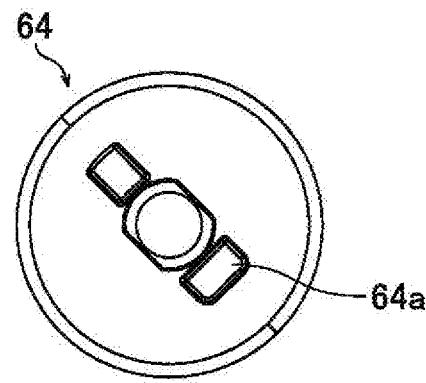
FIG. 8A          FIG. 8B
FIG. 9
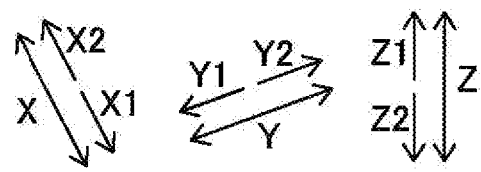
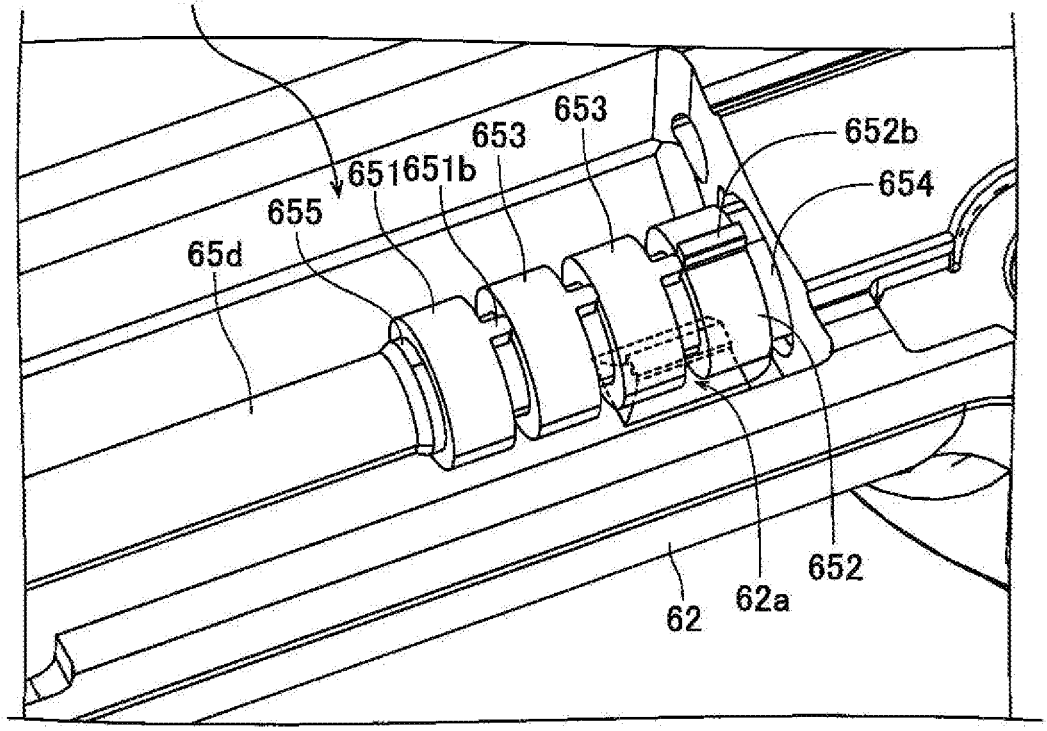

ENDOSCOPE ADAPTOR, ROBOTIC SURGICAL SYSTEM, METHOD OF ADJUSTING ROTATIONAL POSITION USING ENDOSCOPE ADAPTOR

CROSS REFERENCE TO RELATED APPLICATIONS

This application claims priority to Japanese Patent Application No. 2020-061213 filed on Mar. 30, 2020, the entire contents of which are incorporated herein by reference.

BACKGROUND

The disclosure may relate to an endoscope adaptor, a robotic surgical system, and a method of adjusting a rotational position using an endoscope adaptor, and may especially relate to an endoscope adaptor that rotatably supports an endoscope, a robotic surgical system including the endoscope adaptor, and a method of adjusting a rotational position using the endoscope adaptor.

In a related art, there is known an endoscope adaptor that rotatably supports an endoscope.

Japanese Patent Application Publication No. 2020-31767 discloses an endoscope adaptor which rotatably supports an endoscope. The endoscope adaptor includes: a base portion detachably connected to a drape adaptor; a holder (endoscope holder) that holds the endoscope to be rotatable; a driven member that is driven to rotate by a rotation drive part (a drive part) of a robot arm via the drape adaptor; and a transmission mechanism that decelerates rotation of the driven member and transmits the decelerated rotation to the holder. That is, the transmission mechanism is configured in such a manner that the rotation of the driven member is decelerated and transmitted to the endoscope holder.

Japanese Patent Application Publication No. 2020-31767 also discloses a robotic surgical system capable of rotating the rotation drive part of the robot arm to rotate the endoscope by rotating an operation handle.

SUMMARY

Here, in surgery using such a robotic surgical system disclosed in Japanese Patent Application Publication No. 2020-31767, there may be a desire to position the drive part of the robot arm to a home position in a rotatable angle range of the drive part and to position the endoscope to a home position in a rotatable angle range of the endoscope at an initial stage of the surgery after the endoscope is attached to the robot arm, in order to make the field of view of the endoscope in the same state, or in order to equalize the left and right rotatable amounts of the operation handle upon rotating the endoscope. Specifically, in such a robotic surgical system disclosed in Japanese Patent Application Publication No. 2020-31767 in which the endoscope adaptor is equipped with the transmission mechanism that decelerates and transmits the rotation of the drive part of the robot arm to the endoscope holder, it may be difficult to position the endoscope and the drive part of the robot arm to their home positions in the rotatable angle ranges thereof, respectively.

An object of an embodiment of the disclosure may be to provide an endoscope adaptor, a robotic surgical system, and a method of adjusting a rotational position using an endoscope adaptor that are capable of positioning an endoscope and a drive part of a robot arm to their home positions in rotatable angle ranges thereof, respectively.

A first aspect of the disclosure may be an endoscope adaptor to be connected to a robot arm of a robotic surgical system. The endoscope adaptor may include: an endoscope holder configured to rotatably hold an endoscope; and a base portion that includes: an attachment portion to be attached to the robot arm; a driven member configured to be driven to rotate by the drive part of the robot arm; and a transmission mechanism configured to decelerate and transmit rotation of the driven member to the endoscope holder. The transmission mechanism includes a drive transmission shaft configured to be rotated by the rotation of the driven member, a first linkage member configured to rotate integrally with the drive transmission shaft, and a second linkage member being rotatable with respect to the drive transmission shaft and configured to rotate with the first linkage member in a linked manner. The base portion includes a stopper configured to come in contact with the second linkage member to stop rotation of the drive transmission shaft.

In the endoscope adaptor according to the first aspect of the disclosure, the transmission mechanism includes the drive transmission shaft that is configured to be rotated by the rotation of the driven member, the first linkage member that rotates integrally with the drive transmission shaft, and the second linkage member being rotatable with respect to the drive transmission shaft and configured to rotate with the first linkage member in the linked manner, and the base portion includes the stopper configured to come in contact with the second linkage member to stop the rotation of the drive transmission shaft. With this configuration, the driven member can be rotated until the second linkage member that rotates along with the first linkage member comes in contact with the stopper and thus can be rotated up to and stopped at a mechanical end (a mechanical movement limit) for the driven member. Therefore, in a case where a home position of the driven member is predetermined with respect to the rotatable angle range of the driven member (i.e., the range between both mechanical ends for the driven member), the driven member can be moved from one of the mechanical ends of the driven member to the predetermined home position based on the relationship between the rotatable angle range of the driven member and the predetermined home position of the driven member. That is, in the robot arm including the drive part configured to drive the driven member to rotate, the rotational position of the drive part when the driven member is located at the home position can be set as a home position of the drive part (the drive part can be set to the home position of the drive part). Further, by positioning the driven member to the home position of the driven member, the endoscope, which is held by the endoscope holder to which the rotation of the driven member is transmitted, can also be positioned to a home position of the endoscope. As a result, it is possible to provide the endoscope adaptor that is capable of setting the rotational positions of the endoscope and the drive part of the robot arm to the home positions thereof, after the endoscope is attached to the robot arm, for example.

A second aspect of the disclosure may be a robotic surgical system. The robotic surgical system may include: a robot arm; and an endoscope adaptor connected to the robot arm; and a controller that controls a drive part of the robot arm. The endoscope adaptor includes: an endoscope holder that rotatably holds an endoscope; and a base portion that includes: an attachment portion attached to the robot arm; a driven member configured to be driven to rotate by the drive part of the robot arm; and a transmission mechanism configured to decelerate and transmit rotation of the driven member to the endoscope holder. The transmission mechanism includes: a drive transmission shaft that is configured to be rotated by the rotation of the driven member; a first linkage member configured to rotate integrally with the drive transmission shaft; and a second linkage member being rotatable with respect to the drive transmission shaft and configured to rotate with the first linkage member in a linked manner. The base portion includes a stopper configured to come in contact with the second linkage member to stop rotation of the drive transmission shaft. The controller is configured to control, based on a rotational position of the drive part of the robot arm when the second linkage member comes in contact with the stopper and thus the rotation of the drive transmission shaft is stopped, to rotationally position the drive part to a home position of the drive part.

In the second aspect of the disclosure, the transmission mechanism has the configuration same as in the endoscope adaptor according to the first aspect. With this configuration, like the endoscope adaptor according to the first aspect, the driven member can be rotated up to and stopped at the mechanical end (the mechanical movement limit) for the driven member. Further, in the robotic surgical system according to the second aspect, the controller, which controls the drive part of the robot arm, is configured to control to rotationally position the drive part to the home position of the drive part, based on the rotational position of the drive part of the robot arm when the rotation of the drive transmission shaft is stopped. With this, by the control of the controller, the drive part can be set to the home position of the drive part, based on the rotational position of the drive part when the driven member is located at the mechanical end of the driven member. That is, in the case where the home position of the driven member is predetermined with respect to the rotatable angle range of the driven member (i.e., the range between one of the mechanical ends of rotation of the driven member and the other of the mechanical ends of rotation of the driven member), the drive part can be rotationally positioned to the home position thereof by rotating the drive part to move the driven member from the mechanical end for the driven member to the predetermined home position of the driven member based on the relationship between the rotatable angle range of the driven member and the predetermined home position of the driven member. Further, by positioning the driven member to the home position of the driven member, the endoscope, which is held by the endoscope holder to which the rotation of the driven member is transmitted, can also be positioned to the home position of the endoscope. As a result, it is possible to provide the robotic surgical system that is capable of adjusting the rotational positions of the endoscope and the drive part of the robot arm to the home positions thereof, after the endoscope is attached to the robot arm, for example.

A third aspect of the disclosure may be a method of adjusting a rotational position using an endoscope adaptor to be attached to a robot arm of a robotic surgical system.

The method may include: (i) preparing an endoscope adaptor that includes: an endoscope holder configured to rotatably hold the endoscope; and a base portion, wherein the base portion includes: an attachment portion to be attached to the robot arm; a driven member that is provided to the attachment portion and configured to be driven to rotate by a drive part of the robot arm; and a transmission mechanism that includes a drive transmission shaft configured to be rotated by the rotation of the driven member and is configured to decelerate and transmit the rotation of the driven member to the endoscope holder; (ii) rotating the drive transmission shaft by rotating the driven member by the drive part of the robot arm after the endoscope adaptor is attached to the robot arm; (iii) stopping the rotation of the drive transmission shaft by rotating the driven member up to a mechanical end of the driven member; and (iv) after the stopping of the rotation of the drive transmission shaft, rotationally positioning the drive part to a home position of the drive part, based on a rotational position of the drive part of the robot arm when the rotation of the drive transmission shaft is stopped.

In the method of adjusting the rotational position using the endoscope adaptor according to the third aspect of the disclosure, after the endoscope adaptor is attached to the robot arm, the driven member is rotated by the drive part of the robot arm to rotate the drive transmission shaft, and the driven member is rotated up to the mechanical end of the driven member to stop the rotation of the drive transmission shaft. As described above, in the method of adjusting the rotational position using the endoscope adaptor according to the third aspect of the disclosure, after the rotation of the drive transmission shaft is stopped, the drive part is rotationally positioned to the home position of the drive part, based on the rotational position of the drive part of the robot arm when the rotation of the drive transmission shaft is stopped. With this, like the robotic surgical system according to the second aspect, the drive part can be rotationally positioned to the home position of the drive part, based on the rotational position of the drive part when the driven member is located at the mechanical end of the driven member, as a reference point. That is, by rotating the drive part to rotate the driven member from the mechanical end to the home position of the driven member, the drive part can be positioned to the home position of the drive part and the endoscope, which is held by the endoscope holder to which the rotation of the driven member is transmitted, can also be positioned to the home position of the endoscope. As a result, it is possible to set the endoscope and the drive part of the robot arm to the home positions in the rotatable angle ranges thereof, after the endoscope is attached to the robot arm, for example.

BRIEF DESCRIPTION OF THE DRAWINGS

FIG. 8A is a diagram illustrating a plan view of a state where a driven member of the endoscope adaptor is disposed at a home position according to an embodiment;

FIG. 8B is a diagram illustrating a plan view of a state where the driven member of the endoscope adaptor is disposed at a mechanical end according to an embodiment;

FIG. 9 is a diagram illustrating a perspective view of a rotational position adjustment mechanism of the endoscope adaptor according to an embodiment;

DETAILED DESCRIPTION

Figure 1:
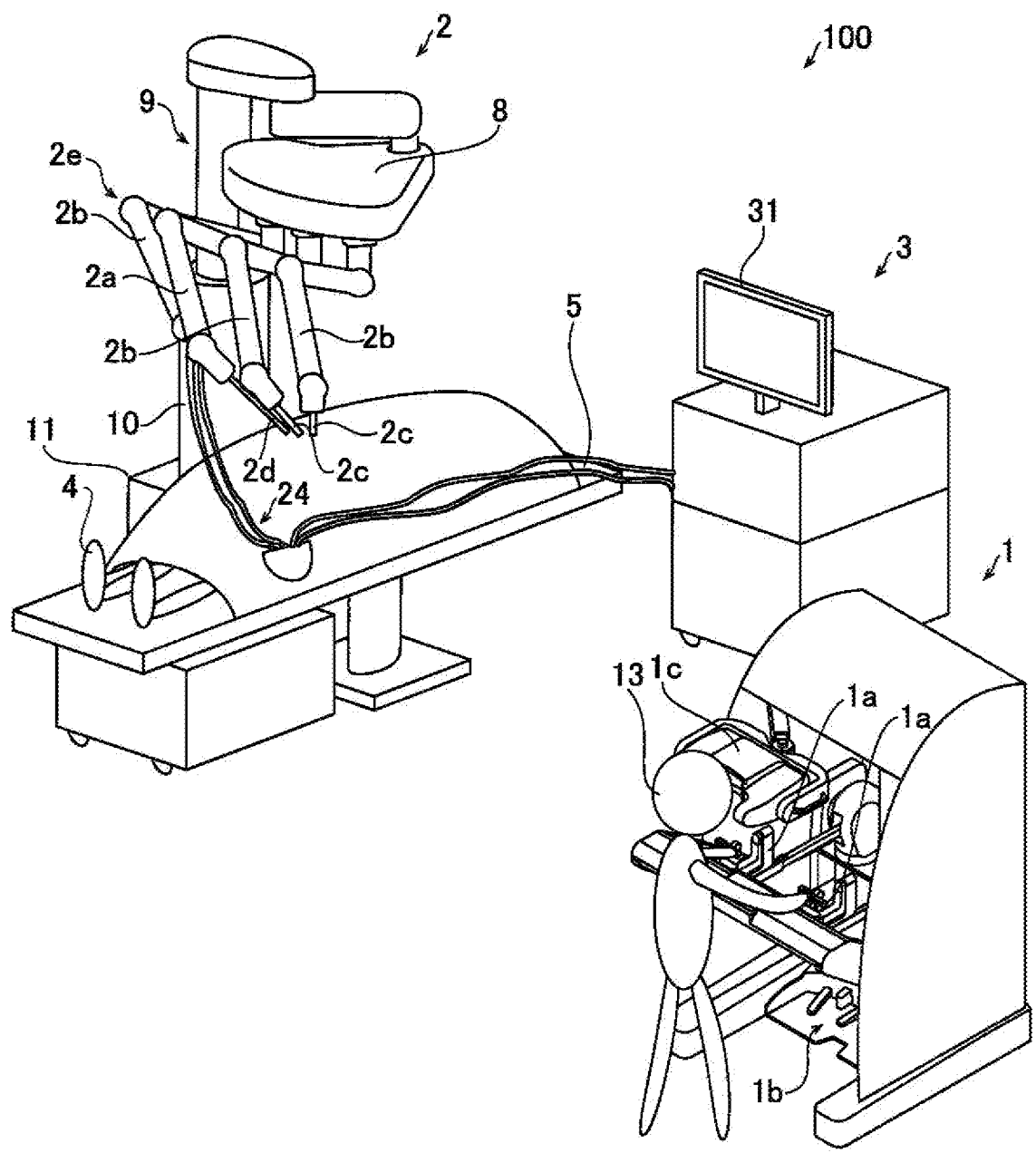
FIG. 1 is a diagram illustrating an overview of a robotic surgical system according to an embodiment.

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

(Configuration of Robotic Surgical System)

A configuration of a robotic surgical system 100 according to an embodiment of the disclosure is described with reference to FIGS. 1 and 2.

As illustrated in FIG. 1, the robotic surgical system 100 includes a remote control apparatus 1, a patient-side apparatus 2, and an image processing apparatus 3.

The remote control apparatus 1 is provided to remotely control medical equipment provided for the patient-side apparatus 2. When an operator 13, as a surgeon, inputs an action mode instruction to be executed by the patient-side apparatus 2, to the remote control apparatus 1, the remote control apparatus 1 transmits the action mode instruction to the patient-side apparatus 2 through a controller.

In response to the action mode instruction transmitted from the remote control apparatus 1, the patient-side apparatus 2 operates medical equipment, including an endoscope 2d attached to a robot arm 2a and surgical instruments 2c attached to robot arms 2b. The image processing apparatus 3 transmits an image of a surgical field captured by the endoscope 2d to the remote control apparatus 1 or the like. This allows minimally invasive surgery.

The patient-side apparatus 2 constitutes an interface to perform a surgery for a patient 4. The patient-side apparatus 2 is positioned beside an operation table 5 on which the patient 4 is laid. The patient-side apparatus 2 includes plural robot arms 2e. One 2a of the robot arms 2e holds the endoscope 2d while the other robot arms 2b hold the surgical instruments 2c. The patient-side apparatus 2 includes an endoscope adaptor 6 (see FIG. 3) for attaching the endoscope 2d to the robot arm 2a and a drape adaptor 7 (see FIG. 3) for attaching a drape 12 (see FIG. 3) to the robot arm 2a. Note that the drape adaptor 7 also functions an adaptor for attaching the endoscope adaptor 6 or the surgical instrument 2c to the robot arm 2b.

The robot arms 2e are commonly supported by a platform 8. Each of the plural robot arms 2e includes plural joints. Each joint includes a driver provided with a servo-motor and a position detector such as an encoder. The robot arms 2e are configured so that the medical equipment attached to each robot arm 2e is controlled by a driving signal given through the controller and performs a desired movement.

The platform 8 is supported by a positioner 9 placed on the floor of an operation room. The positioner 9 includes a column 10 and a base 11. The column 10 includes an elevating shaft adjustable in the vertical direction. The base 11 includes wheels and is movable on the floor surface.

To the distal end of the robot arm 2a, the endoscope 2d as the medical equipment is detachably attached. The endoscope 2d captures an image in the body cavity of the patient 4. The captured image is outputted to the remote control apparatus 1 through the image processing apparatus 3. The endoscope 2d may be a 3D endoscope capable of capturing a three-dimensional image or a 2D endoscope. In surgeries using the patient-side apparatus 2, the robot arm 2e introduces the endoscope 2d into the body of the patient 4 through a trocar placed on the body surface of the patient 4. The endoscope 2d is then located near the surgery site.

The remote control apparatus 1 constitutes an interface with the operator 13. The remote control apparatus 1 is an apparatus that allows the operator 13 to operate medical equipment attached to the robot arms 2e. Specifically, the remote control apparatus 1 is configured to transmit action mode instructions which are inputted by the operator 13 and are to be executed by the surgical instruments 2c and endoscope 2d, to the patient-side apparatus 2 through the controller. The remote control apparatus 1 is installed beside the operation table 5 so that the operator 13 can see the condition of the patient 4 very well while operating the remote control apparatus 1, for example. The remote control apparatus 1 may be configured to transmit action mode instructions wirelessly and installed in a room different from the operation room where the operation table 5 is installed.

The action modes to be executed by the surgical instruments 2c include modes of actions to be taken by each surgical instrument 2c (a series of positions and postures) and actions to be executed by the function of each surgical instrument 2c. When the surgical instrument 2c is a pair of grasping forceps, for example, the action modes to be executed by the surgical instrument 2c include roll and pitch positions of the wrist of an end effector and actions to open and close the jaws. When the surgical instrument 2c is a high-frequency knife, the action modes to be executed by the surgical instrument 2c include vibration of the high-frequency knife, specifically, supply of current to the high-frequency knife. When the surgical instrument 2c is a snare wire, the action modes to be executed by the surgical instrument 2c include a capturing action and an action to release the captured object. Further the action modes may include an action to supply current to a bipolar or monopolar instrument to burn off the surgery site.

The action mode to be executed by the endoscope 2d includes setting of the position and posture of the tip of the endoscope 2d or setting of the zoom magnification of the endoscope 2d, for example.

Figure 2:
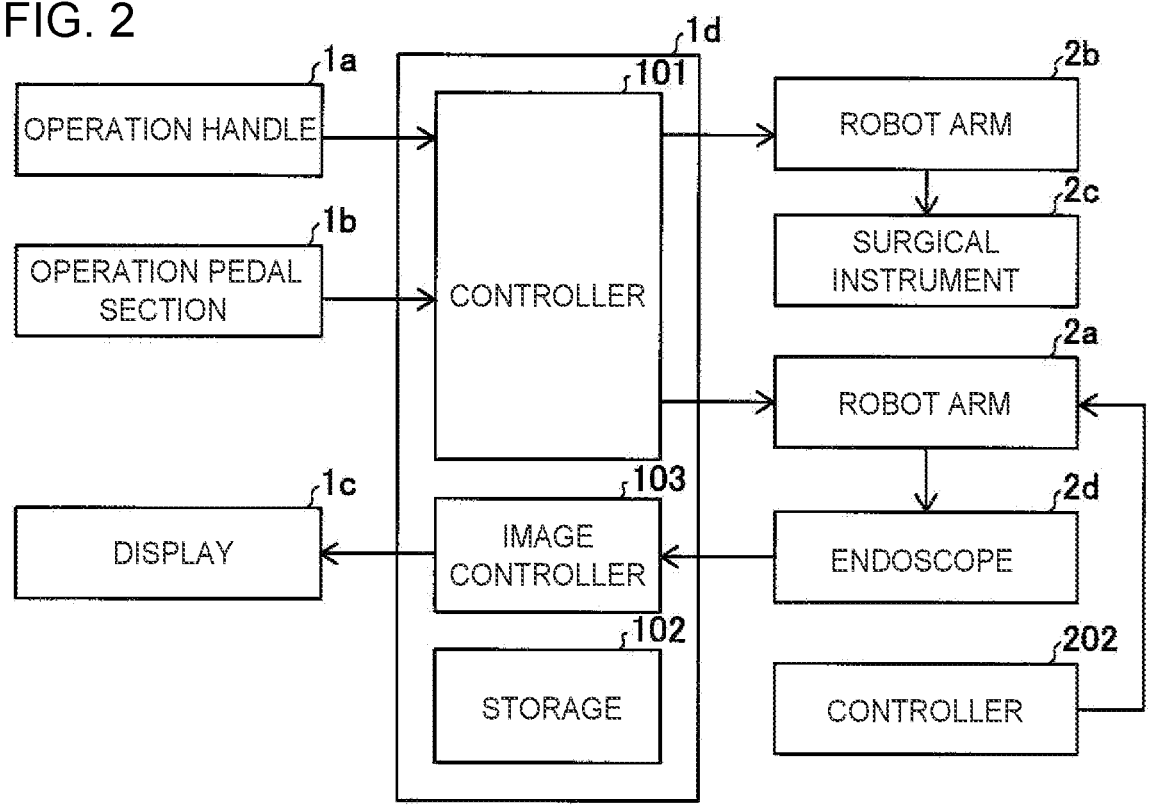
FIG. 2 is a block diagram illustrating a view of a control-related configuration of the robotic surgical system according to an embodiment.

The remote control apparatus 1 includes operation handles 1a, an operation pedal section 1b, a display 1c, and a control apparatus 1d (see FIG. 2).

The operation handles 1a are provided in order to remotely operate medical equipment attached to the robot arms 2e. Specifically, the operation handles 1a accept operations by the operator 13 for operating the medical equipment (the surgical instruments 2c and the endoscope 2d). The operation handles 1a include two operation handles 1a arranged side by side in the horizontal direction. That is, one of the two operation handles 1a is operated by the right hand of the operator 13 while the other of the two operation handles 1a is operated by the left hand of the operator 13.

The operation handles 1a extend from the rear side of the remote control apparatus 1 toward the front side. The operation handles 1a are configured to move in a predetermined three-dimensional operation region. Specifically, the operation handles 1a are configured so as to move up and down, right and left, and forward and rearward.

As illustrated in FIG. 2, the remote control apparatus 1 and patient-side apparatus 2 constitute a master-slave system in terms of controlling movements of the robot arm 2a and the robot arms 2b. The operation handles 1a constitute an operating part on the master side in the master-slave system, and the robot arms 2a and 2b holding the medical equipment constitute an operating part on the slave side. When the operator 13 operates the operation handles 1a, the movement of the robot arm 2a or 2b is controlled so that the distal end portion (the endoscope 2d) of the robot arm 2a or the distal end portion (the end effector of the surgical instrument 2c) of the robot arm 2b moves following the movement of the operation handles 1a.

The patient-side apparatus 2 controls the movement of the robot arms 2b in accordance with the set motion scaling ratio. When the motion scaling ratio is set to ½, for example, the end effectors of the surgical instruments 2c move ½ of the movement distance of the operation handles 1a. This allows precise fine surgery.

As illustrated in FIG. 1, the operation pedal section 1b includes plural pedals that execute functions of the medical equipment. The plural pedals include a coagulation pedal, a cutting pedal, a camera pedal, and a clutch pedal. The plural pedals are operated by a foot of the operator 13.

The coagulation pedal enables the surgical instrument 2c to coagulate the surgery site. Specifically, when the coagulation pedal is operated, voltage for coagulation is applied to the surgical instrument 2c to coagulate the surgery site. The cutting pedal enables the surgical instrument 2c to cut the surgery site. Specifically, the cutting pedal is operated to apply voltage for cutting to the surgical instrument 2c and cut the surgery site.

The camera pedal is used to control the position and orientation of the endoscope 2d that captures images within the body cavity. Specifically, the camera pedal enables control of the endoscope 2d by the operation handle 1a. That is, the position and orientation of the endoscope 2d are controllable by the operation handles 1a while the camera pedal is being pressed. The endoscope 2d is controlled by using both of the right and left operation handles 1a, for example. Specifically, when the operator 13 rotates the right and left operation handles 1a about the middle point between the right and left operation handles 1a, the endoscope 2d is rotated. When the operator 13 presses the right and left operation handles 1a together, the endoscope 2d goes further into the body cavity. When the operator 13 pulls the right and left operation handles 1a together, the endoscope 2d retracts. When the operator 13 moves the right and left operation handles 1a together up, down, right, and left, the endoscope 2d moves up, down, right, and left, respectively.

The clutch pedal is used to temporarily disconnect operation-related connection between the operation handles 1a and the robot arms 2e to stop movement of the surgical instruments 2c. Specifically, when the clutch pedal is being pressed, the robot arms 2e of the patient-side apparatus 2 do not work even if the operation handles 1a are operated. For example, when the operation handles 1a are operated and moved to the edge of the range of movement, the operator 13 operates the clutch pedal to temporarily disconnect the operation-related connection and then returns the operation handles 1a to the center of the range of movement. When the operator 13 stops operating the clutch pedal, the operation handles 1a are again connected to the robot arms 2e so that the operator 13 can restart the operation for the operation handles 1a around the center thereof.

The display 1c (or a display device) is configured to display images captured by the endoscope 2d. The display 1c is composed of a scope type display or a non-scope type display. The scope type display is a display configured in such a manner that the operator 13 looks into the display. The non-scope type display is a display like an open-type display that includes a flat screen and the operator 13 is able to see without looking into, such as normal displays for personal computers.

When the scope type display is attached, the scope type display displays 3D images captured by the endoscope 2d attached to the robot arm 2e of the patient-side apparatus 2. When the non-scope type display is attached, the non-scope type display also displays 3D images captured by the endoscope 2d provided for the patient-side apparatus 2. The non-scope type display may display 2D images captured by the endoscope 2d provided for the patient-side apparatus 2.

As illustrated in FIG. 2, the control apparatus 1d includes a controller 101, a storage 102, and an image controller 103, for example. The controller 101 includes a calculator or a processor such as a CPU or the like. The storage 102 includes a memory, such as a ROM, a RAM, or the like. The control apparatus 1d may be composed of a single controller performing centralized control or may be composed of plural controllers that perform decentralized control in cooperation with each other.

The controller 101 determines whether an action mode instruction inputted by the operation handles 1a is to be executed by the robot arms 2b or to be executed by the endoscope 2d, depending on the state of the operation pedal section 1b. When determining that the action mode instruction inputted by the operation handles 1a is to be executed by any one of the surgical instruments 2c, the controller 101 transmits the action mode instruction to the corresponding robot arm 2b. The robot arm 2b is thereby driven for control of movement of the surgical instrument 2c attached to the robot arm 2b.

When determining that the action mode instruction inputted by the operation handles 1a is to be executed by the endoscope 2d, the controller 101 transmits the action mode instruction to the robot arm 2a. The robot arm 2a is thereby driven for controlling movement of the endoscope 2d attached to the robot arm 2a.

The storage 102 stores control programs corresponding to the types of the surgical instruments 2c, for example. The controller 101 reads the stored control programs according to the types of the attached surgical instruments 2c. The action mode instructions from the operation handles 1a and/or the operation pedal section 1b of the remote control apparatus 1 thereby cause the respective surgical instruments 2c to perform proper motions.

The image controller 103 transmits an image acquired by the endoscope 2d to the display 1c. The image controller 103 performs processing and correcting the images when needed.

The image processing apparatus 3 is configured to transmit the image obtained from the endoscope 2d to the remote control apparatus 1 (see FIG. 1) and display the image obtained from the endoscope 2d. The image processing apparatus 3 performs processing and correcting the image obtained from the endoscope 2d when needed. Specifically, the image processing apparatus 3 includes an external monitor 31. The external monitor 31 is configured to be display the image captured by the endoscope 2d. The external monitor 31 is an open-type display section that includes a flat screen, such as normal displays for personal computers.
(Configurations of Drape Adaptor, Endoscope Adaptor, and Endoscope)

With reference to FIGS. 3 to 13, configurations of the drape adaptor 7, the endoscope adaptor 6, and the endoscope 2d according to an embodiment are described.

Figure 3:
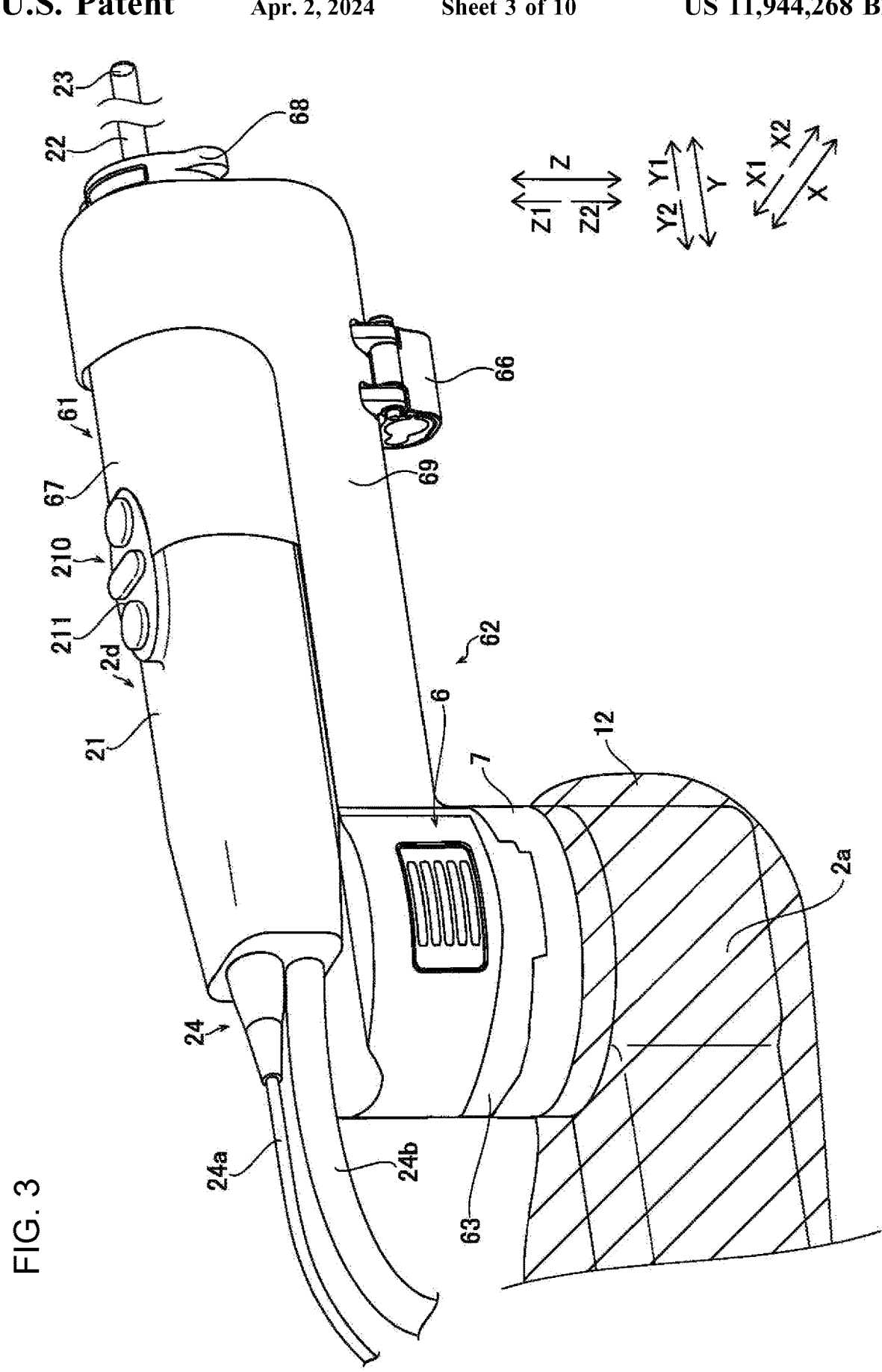
FIG. 3 is a diagram illustrating a perspective view of a state where an endoscope is attached to a robot arm through an endoscope adaptor according to an embodiment.

As illustrated in FIG. 3, the robot arms 2e are used in a clean area and thus are covered with the drapes 12. In operation rooms, clean technique is used in order to prevent surgical incision sites and the medical equipment from being contaminated by pathogen, foreign matters, or the like. The clean technique defines a clean area and a contaminated area, which is outside the clean area. The surgery sites are located in the clean area. Members of the surgical team, including the operator 13 (see FIG. 1), make sure that only sterile objects are placed in the clean area during surgery and perform sterilization for an object which is to be moved to the clean area from the contaminated area. Similarly, when the members of the surgical team including the operator 13 place their hands in the contaminated area, the members sterilize their hands before directly touching objects located in the clean area. Instruments used in the clean area are sterilized or are covered with the sterile drapes 12.

The drape 12 is arranged between the drape adaptor 7 and the robot arm 2a (2b (see FIG. 1)). The drape adaptor 7 is attached to the robot arm 2e with the drape 12 being sandwiched between the drape adaptor 7 and the robot arm 2e. Specifically, the drape adaptor 7 is an adaptor that puts the drape 12 between the drape adaptor 7 and the robot arm 2e.

In the following description, a direction in which an attachment portion 63 (described later) of the endoscope adaptor 6 and the endoscope 2d are arranged is referred to as a Z direction (Z axis). Along the Z direction, the endoscope 2d side and the attachment portion 63 side are respectively referred to as a Z1 direction (Z1 side) and a Z2 direction (Z2 side). Further, a direction in which a base portion 62 (described later) of the endoscope adaptor 6 extends is referred to as a Y direction (Y axis). Along the Y direction, a direction in which the endoscope 2d is inserted into the endoscope adaptor 6 is referred to as a Y1 direction (Y1 side) and the opposite direction of the Y1 direction is referred to as a Y2 direction (Y2 side). Further, a direction orthogonal to the Y direction and the Z direction is referred to as an X direction (X axis). One side along the X direction is referred as an X1 direction (X1 side), and the other side along the X direction is referred to as an X2 direction (X2 side).

The endoscope 2d is rotatably supported by the endoscope adaptor 6. The endoscope 2d is detachably attached to the endoscope adaptor 6. The endoscope 2d includes a main body 21, an elongate insertion part 22, and an imaging part 23. The endoscope 2d is supported by the endoscope adaptor 6 to be rotatable about a rotation axis C1 (see FIG. 5) along an extending direction (Y direction) of the insertion part 22. The rotation axis C1 is substantially aligned with the center line of the insertion part 22.

The main body 21 has an elongate shape extending in the Z direction. The insertion part 22 is connected to one end of the main body 21, and cables 24 are connected to the other end of the main body 21. The cables 24 includes a camera cable 24a for transmitting data of an image captured by the endoscope 2d and a light cable 24b for irradiating light when imaging the inside of the body cavity of the patient with the endoscope 2d. A diameter of the camera cable 24a is smaller than a diameter of the light cable 24b. The camera cable 24a is provided on the Z1 side with respect to the light cable 24b. Note that as the endoscope 2d, a general-purpose endoscope may be used, or an endoscope dedicated for being attached to the robot arm 2a may be used.

The insertion part 22 is a part that is to be inserted in the body of the patient 4. The insertion part 22 has a hardness that tends to be difficult to be deformed. That is, the endoscope 2d is a rigid endoscope. The insertion part 22 is to be inserted into the body of the patient 4 through a trocar placed on the body surface of the patient 4. To a distal end of the insertion part 22 (the end opposite to the side of the main body 21 of the endoscope), the imaging part 23 is provided. Accordingly, the imaging part 23 can be placed in the body of the patient 4 to capture an image of the surgical site in the body.

The imaging part 23 can capture an image by a single eye or plural eyes. That is, the imaging part 23 can image an object from a single position or multiple positions. The imaging part 23 is provided with illumination. The illumination is turned on to irradiate light to the imaging target upon imaging.

Figure 4:
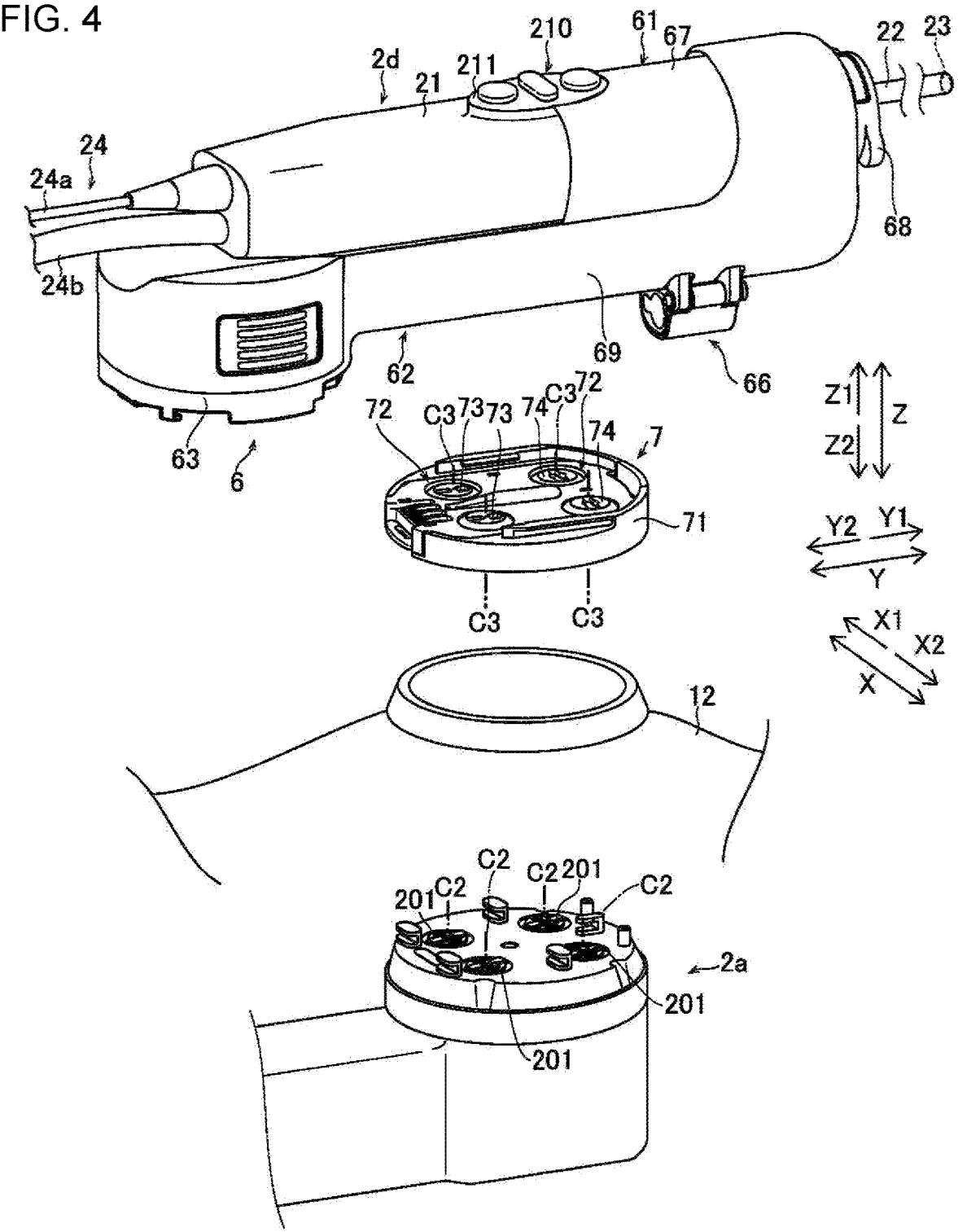
FIG. 4 is a diagram illustrating an exploded perspective view of a state where a drape adaptor and the endoscope adaptor are detached from the robot arm according to an embodiment.
Figure 5:
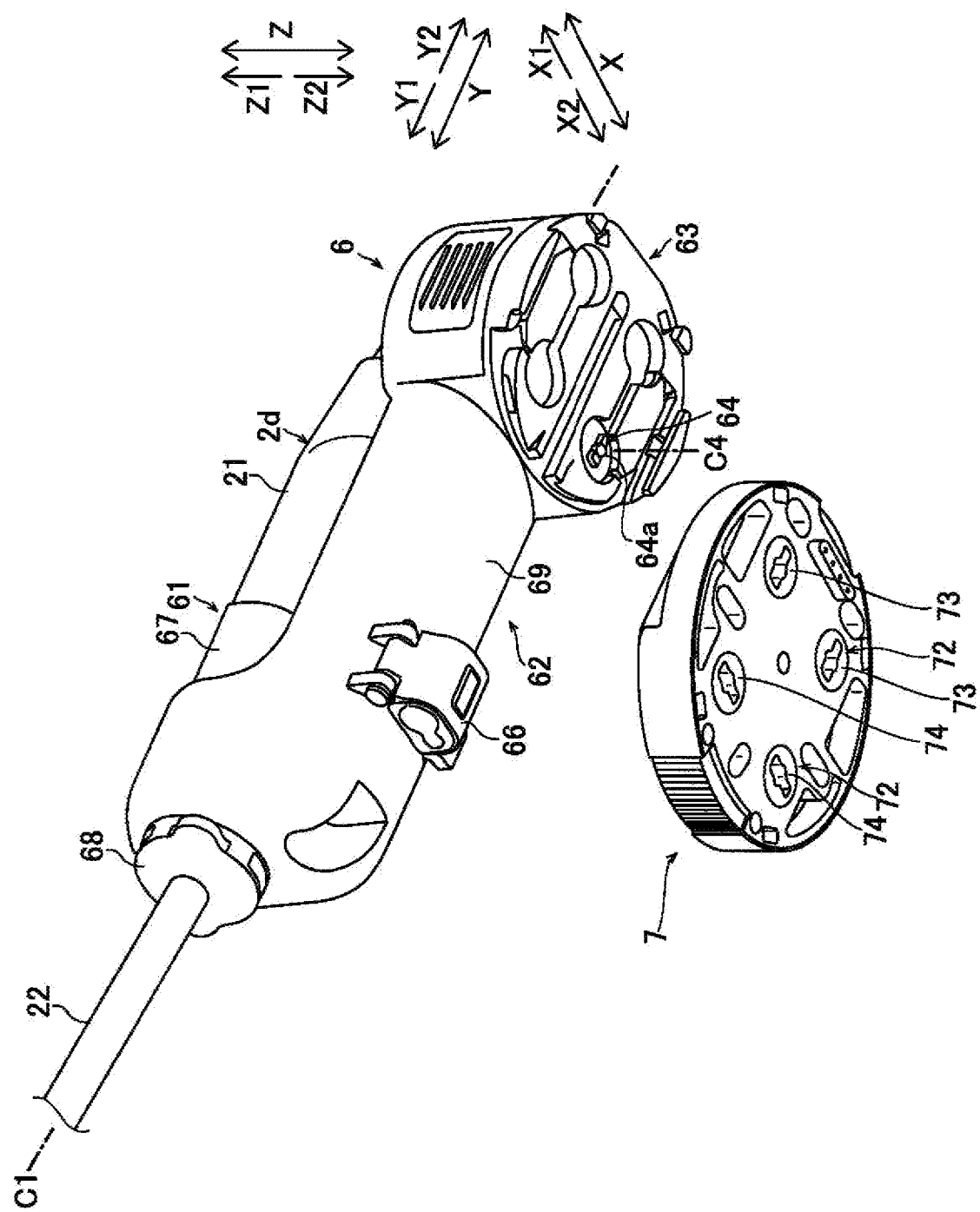
FIG. 5 is a diagram illustrating an exploded perspective view of the endoscope adaptor and the drape adaptor according to an embodiment as seen from below.

As illustrated in FIGS. 4 and 5, in a state where the endoscope 2d is attached to the endoscope adaptor 6, the endoscope 2d is connected to the robot arm 2a of the robotic surgical system 100 through the drape adaptor 7. The robot arm 2a transmits driving force to the endoscope adaptor 6 through the drape adaptor 7 to rotate the endoscope 2d. Specifically, the robot arm 2a is provided with drive parts 201.

Figure 7:
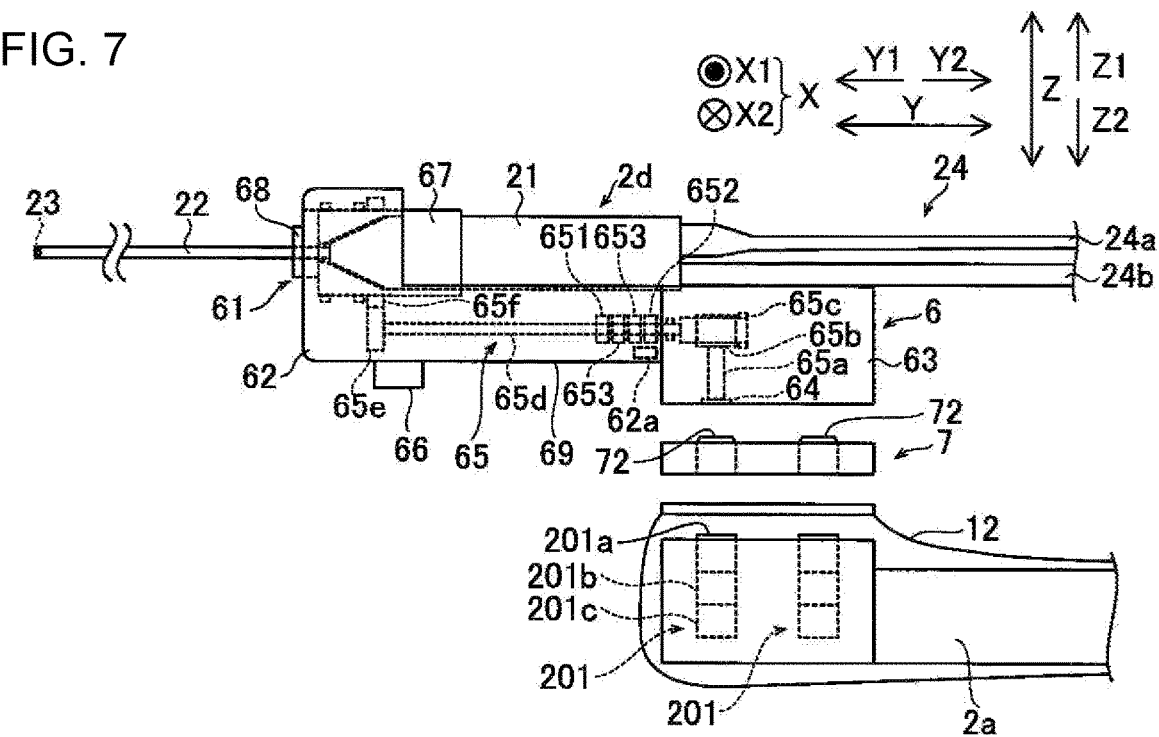
FIG. 7 is a diagram illustrating a side view of a transmission mechanism of the endoscope adaptor according to an embodiment.

As illustrated in FIG. 7, each of the drive parts 201 includes an engagement projection 201a, a motor 201b, and an encoder 201c. The engagement projection 201a is configured to be driven by the motor 201b as a drive source to rotate about a rotation axis C2 extending in the Z direction. The encoder 201c detects rotational positions of the motor 201b and the engagement projection 201a. As the encoder 201c, an absolute rotary encoder is preferably used in order to detect the rotational position of the motor 201b.

As illustrated in FIGS. 4 and 5, the drape adaptor 7 includes a base body 71 and plural drive transmission members 72. The drive transmission members 72 include first drive transmission members 73 arranged on the Y2 side and second drive transmission members 74 arranged on the Y1 side. The drive transmission members 72 are rotatably provided in the base body 71. Specifically, the drive transmission members 72 are provided to be rotatable about rotation axes C3 extending in the Z direction. The drive transmission member 72 transmits driving force of the drive part 201 of the robot arm 2a to a driven member 64 of the endoscope adaptor 6.

As illustrated in FIGS. 4 and 5, the endoscope adaptor 6 includes an endoscope holder 61 that rotatably holds the endoscope, and a base portion 62 to which the endoscope holder 61 is attached. In an embodiment, the endoscope holder 61 is attached to the base portion 62 such that the endoscope holder 61 is rotatable with respect to the base portion 62.

Figure 6:
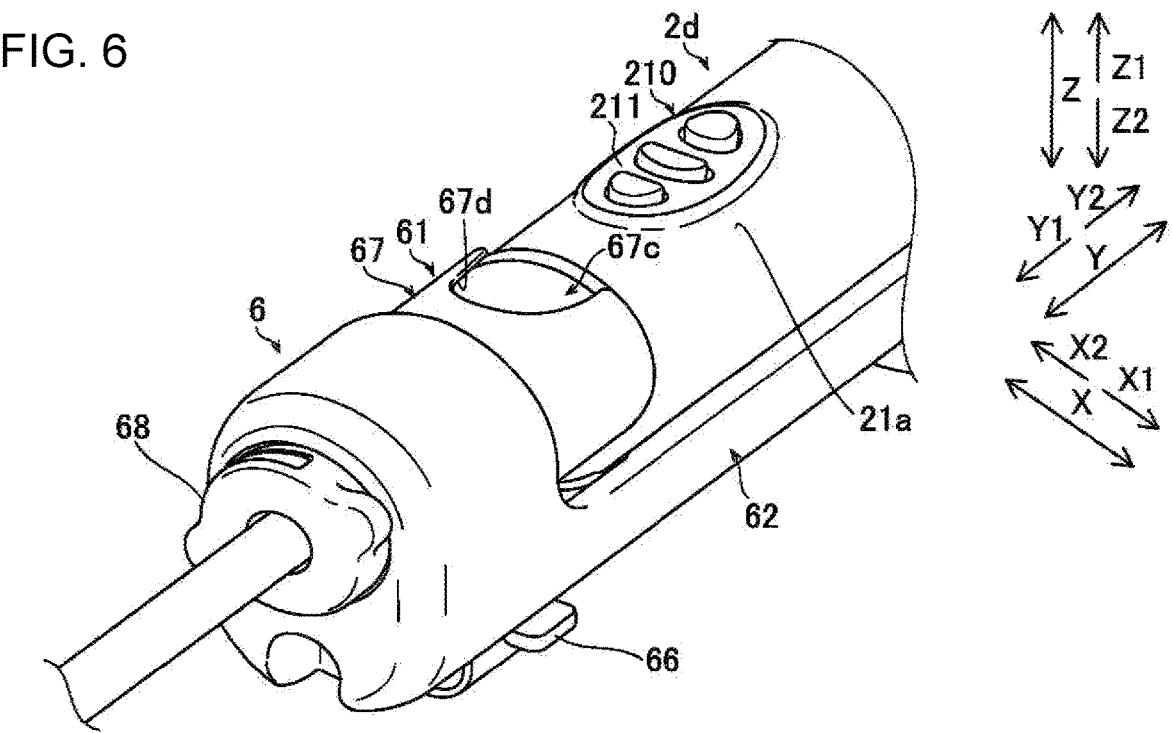
FIG. 6 is a diagram illustrating a perspective view of the endoscope adaptor according to an embodiment.

As illustrated in FIG. 6, the endoscope holder 61 is configured to hold the endoscope 2d. That is, the endoscope holder 61 is configured to attach the endoscope 2d to the base portion 62. Specifically, the endoscope holder 61 includes a holder main body 67 and a lock part 68.

The holder main body 67 has a substantially circular cylindrical shape. The holder main body 67 includes an insertion hole (not illustrated) to which the endoscope 2d is to be inserted. The insertion hole penetrates through the holder main body 67 in the Y direction. The holder main body 67 includes a pair of engagement portions (not illustrated) to attach the lock part 68. The pair of the engagement portions are projected in a direction orthogonal to the Y direction. The holder main body 67 is provided on the Y2 side with respect to the lock part 68.

The endoscope holder 61 includes an engagement portion 67c to be engaged with an engagement portion 210 of the endoscope 2d upon attaching the endoscope 2d. The engagement portion 67c is engaged with an operation part 211 serving as a convex engagement portion 210 projected from an outer circumferential surface 21a of the endoscope 2d and comprise a notch 67d recessed in the endoscope holder 61 toward the Y1 direction (the insertion direction of the endoscope) in which the endoscope 2d is inserted to the endoscope holder 61. The notch 67d is configured to position the endoscope 2d in a state where the engagement portion 67c and the engagement portion 210 are engaged with each other. Accordingly, the endoscope 2d rotates integrally with the endoscope holder 61.

The lock part 68 includes an insertion hole (not illustrated) to which a distal end portion of the main body 21 of the endoscope 2d is inserted. The lock part 68 is configured to be engaged with an engagement portion (not illustrated) of the holder main body 67.

As illustrated in FIGS. 4 and 5, the base portion 62 includes: an attachment portion 63 to be attached to the robot arm 2a via the drape adaptor 7; the driven member 64 that is provided in the attachment portion 63 and is to be driven to rotate by the drive part 201 of the robot arm 2a; and a transmission mechanism 65 to transmit the rotation of the driven member 64 to the endoscope holder 61.

As illustrated in FIG. 4, the attachment portion 63 is provided to detachably connect the endoscope adaptor 6 and the drape adaptor 7. The attachment portion 63 is provided on the Y2 side in the base portion 62. The base portion 62 includes an extension portion 69 extending in the Y1 direction from the attachment portion 63. The driven member 64 is provided to the attachment portion 63.

The driven member 64 of the endoscope adaptor 6 is driven to rotate so as to rotate the endoscope 2d. The number of the drive member 64 provided in the endoscope adaptor 6 is one. The number of the drive parts 201 provided in the robot arm 2a is four. Also, the number of the drive transmission members 72, to be engaged with the drive parts 201, provided in the drape adaptor 7 is four. The engagement projections 201a (see FIG. 7) of the drive parts 201 of the robot arm 2a are engaged with the drive transmission members 72 of the drape adaptor 7. An engagement projection 64a of the driven members 64 of the endoscope adaptor 6 is engaged with one of the drive transmission members 72 of the drape adaptor 7. Therefore, the driven member 64 is driven to rotate by the drive part 201 of the robot arm 2a via the drape adaptor 7.

As illustrated in FIG. 7, the transmission mechanism 65 is configured to transmit the rotation of the driven member 64 to the endoscope holder 61 to rotate the endoscope 2d about the rotation axis C1 (see FIG. 5). The transmission mechanism 65 includes a shaft 65a, a helical tooth gear 65b, a cylindrical worm 65c, a shaft 65d, a gear 65e, and a gear 65f. The shaft 65a is provided to extend linearly in the Z direction. The driven member 64 is connected to an end portion of the shaft 65a on the Z2 side. The helical tooth gear 65b is connected to a Z1 side end portion of the shaft 65a. The helical tooth gear 65b is connected to (meshed with) the cylindrical worm 65c. The shaft 65d is provided to extend linearly in the Y direction. The cylindrical worm 65c is connected to a Y2 side end portion of the shaft 65d. The gear 65e is connected to a Y1 side end portion of the shaft 65d. That is, the gear 65e and the cylindrical worm 65c are coaxially provided to each other. The gear 65e is connected to (meshed with) the gear 65f. The gear 65f is provided to the endoscope holder 61. With this, the rotation of the drive part 201 of the robot arm 2a rotates the endoscope holder 61 and thus rotates the endoscope 2d. Note that the shaft 65d is an example of a drive transmission shaft.

The transmission mechanism 65 is configured in such a manner that the rotation of the driven member 64 is decelerated and transmitted to the endoscope holder 61. That is, the amount of rotation of the endoscope holder 61 (the endoscope 2d) is smaller than the amount of rotation of the driven member 64. Specifically, the transmission mechanism 65 is configured in such a manner that the rotation of the drive part 201 is increased by approximately 1.6 times and transmitted to the shaft 65d by means of the helical tooth gear 65b and the cylindrical worm 65c. That is, the amount of rotation of the shaft 65d is larger than the amount of rotation of the driven member 64. To the contrary, the transmission mechanism 65 is configured in such a manner that the rotation of the shaft 65d is reduced by approximately 6/11 times and transmitted to the endoscope holder 61 by means of the gear 65e and the gear 65f. That is, the amount of rotation of the endoscope holder 61 (the endoscope 2d) is smaller than the amount of rotation of the shaft 65d. Considering the transmission mechanism 65 as a whole, the transmission mechanism 65 is configured in such a manner that the rotation of the driven member 64 is decelerated and transmitted to the endoscope holder 61. That is, the amount of rotation of the endoscope holder 61 (the endoscope 2d) is smaller than the amount of rotation of the driven member 64.

As illustrated in FIG. 5, the endoscope adaptor 6 is configured to bundle the cables 24 (see FIG. 1) by holding the cables 24 that hang down in the Y1 side. A cable holder 66 is configured by a clump mechanism that holds the cables 24 therein. That is, the cable holder 66 holds the cables 24 to arrange the cables 24 at a desired arrangement position.

Here, as illustrated in FIG. 3, the endoscope adaptor 6 is detachably connected to the robot arm 2a of the robotic surgical system 100 (through the drape adaptor 7 holding the drape 12). The endoscope adaptor 6 includes the endoscope holder 61 and the base portion 62. The endoscope holder 61 holds the endoscope 2d to be rotatable. As illustrated in FIG. 3, the base portion 62 includes the attachment portion 63, the driven member 64, and the transmission mechanism 65 (see FIG. 7). The attachment portion 63 is attached (via the drape adaptor 7) to the robot arm 2a (i.e., the drive part 201 (see FIG. 4) of the robot arm 2a). As illustrated in FIG. 7, the driven member 64 is provided on the attachment portion 63 and is rotationally driven by the drive part 201 of the robot arm 2a (via the drape adaptor 7). The transmission mechanism 65 decelerates the rotation of the driven member 64 and transmits the decelerated rotation to the endoscope holder 61. As illustrated in FIG. 9, the transmission mechanism 65 includes: the shaft 65d that is configured to be rotated by the rotation of the driven member 64; a first linkage member 651 that is configured to rotate integrally with the shaft 65d; and a second linkage member 652 that is provided rotatable with respect to the shaft 65d and configured to rotate with the first linkage member 651 in a linked manner. The base portion 62 (i.e., the extension portion 69 of the base portion 62) includes a stopper 62a configured to come in contact with the second linkage member 652 to stop the rotation of the shaft 65d.

In the endoscope adaptor 6 according to an embodiment, the transmission mechanism 65 includes: the shaft 65d that is configured to be rotated by the rotation of the driven member 64; the first linkage member 651 that is configured to rotate integrally with the shaft 65d; and the second linkage member 652 that is provided rotatable with respect to the shaft 65d and is linkable to the first linkage member 651 so as to rotate together with the first linkage member 651 when being linked to the first linkage member 651. Also, the base portion 62 (i.e., the extension portion 69 of the base portion 62) includes the stopper 62a configured to come in contact with the second linkage member 652 to stop the rotation of the shaft 65d. With this configuration, by rotating the driven member 64 until the second linkage member 652, which is rotating with the first linkage member 651 in the linked manner, comes in contact with the stopper 62a, the driven member 64 can be rotated up to and stopped at the mechanical end (the mechanical movement limit) for the driven member 64. Therefore, in a case where a home position (an origin position or an initial position) of the driven member 64 is predetermined with respect to the rotatable angle range of the driven member 64 (i.e., the range between one of the mechanical ends of rotation of the driven member 64 and the other of the mechanical ends of rotation of the driven member 64), the driven member 64 can be moved from one of the mechanical ends of rotation of the driven member 64 to the predetermined home position based on the relationship between the rotatable angle range of the driven member 64 and the predetermined home position of the driven member 64. That is, in the robot arm 2a equipped with the drive part 201 that drives the driven member 64 to rotate, the rotational position of the drive part 201 when the driven member 64 is positioned at the home position of the driven member 64 can be set as the home position of the drive part 201 (the drive part 201 can be rotationally positioned to the home position of the drive part 201). Specifically, in an embodiment, the rotatable angle range of the driven member 64 and the rotatable angle range of the drive part 201 (i.e., the engagement projection 201a of the drive part 201) are both approximately 824 degrees with approximately 412 degrees in the counterclockwise direction (+412 degrees) and approximately 412 degrees in the clockwise direction (−412 degrees). Accordingly, by rotating the drive part 201 (i.e, the engagement projection 201a of the drive part 201) of the robot arm 2a by approximately 412 degrees from the state where the driven member 64 and the drive part 201 (i.e, the engagement projection 201a of the drive part 201) are located at one of the mechanical ends thereof, the driven member 64 and the drive part 201 (i.e, the engagement projection 201a of the drive part 201) are moved to their home positions (the rotational positions of 0 degrees). Further, by positioning the driven member 64 to the home position of the driven member 64, the endoscope 2d, which is held by the endoscope holder 61 to which the rotation of the driven member 64 is transmitted, can also be positioned to the home position of the endoscope 2d. As a result, it is possible to provide the endoscope adaptor 6 that is capable of adjusting the rotational positions of the endoscope 2d and the drive part 201 of the robot arm 2a to the home positions thereof in the state where the endoscope 2d is attached to the robot arm 2a.

Figure 11:
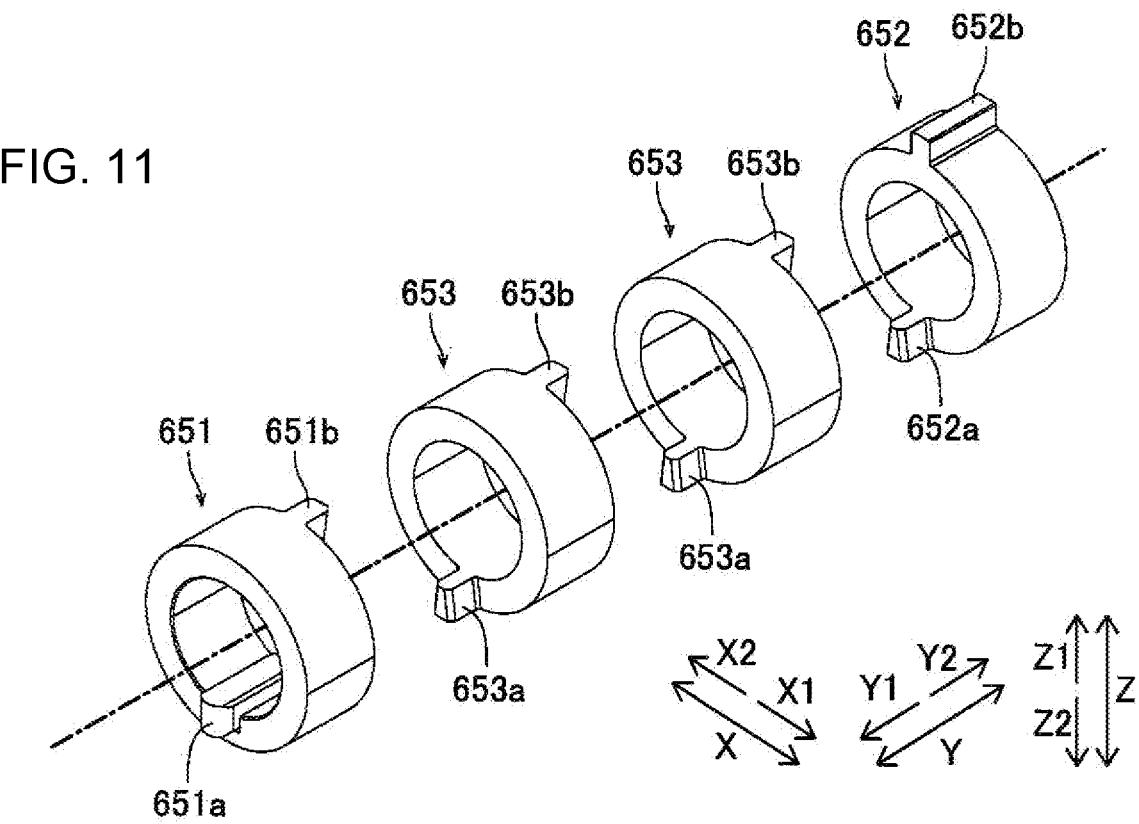
FIG. 11 is a diagram illustrating a perspective view of a state where the rotational position adjustment mechanism of the endoscope adaptor is disassembled according to an embodiment.

Specifically, as illustrated in FIG. 11, each of the first linkage member 651 and the second linkage member 652 has an annular shape, as seen along the Y direction, formed with a through hole through which the shaft 65d passes. That is, each of the first linkage member 651 and the second linkage member 652 is formed in a ring shape.

Figure 10:
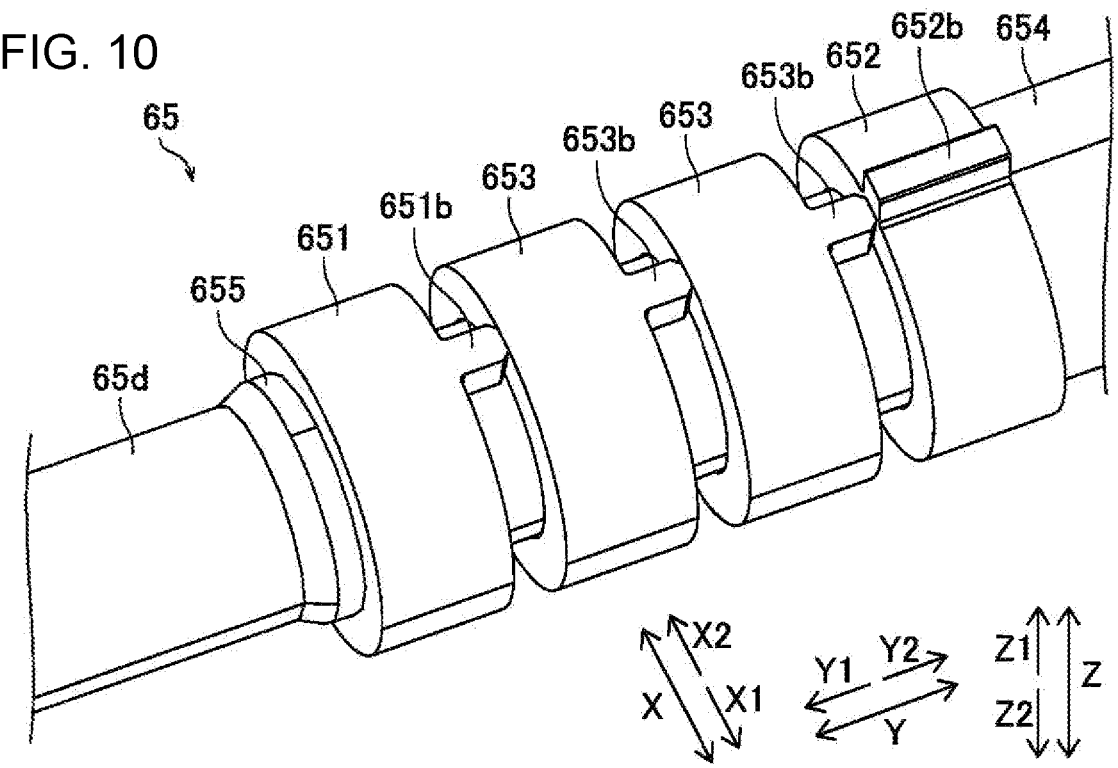
FIG. 10 is a diagram illustrating an enlarged perspective view of the rotational position adjustment mechanism of the endoscope adaptor according to an embodiment.
Figure 12:
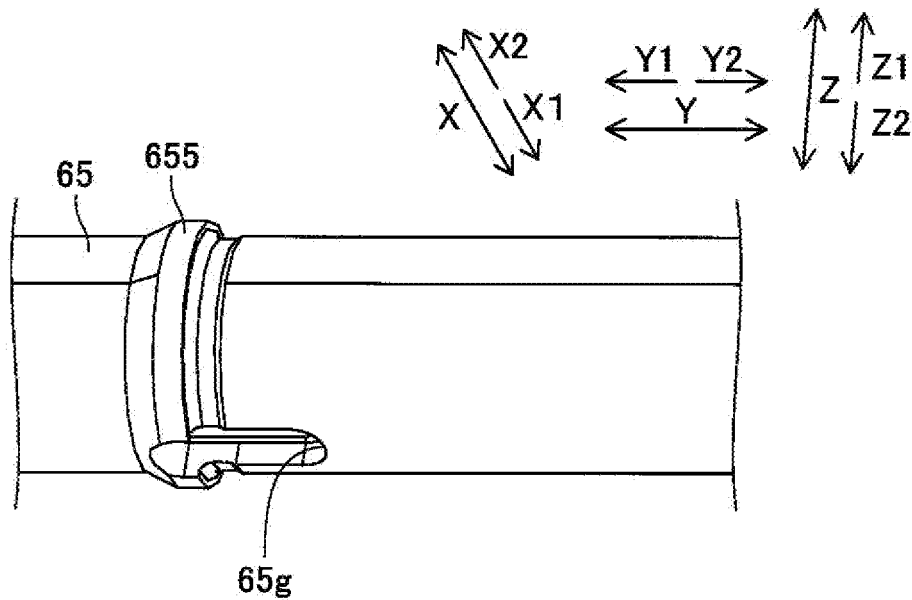
FIG. 12 is a diagram illustrating a perspective view of a key groove of a drive transmission shaft of the endoscope adaptor according to an embodiment.

As illustrated in FIG. 12, the shaft 65d is formed with a key groove 65g. As illustrated in FIG. 11, the first linkage member 651 is formed with a key 651a engaged with the key groove 65g. Thus, the first linkage member 651 is fixed to the shaft 65d and rotates integrally with the shaft 65d. Note that as illustrated in FIG. 12, on the Y1 side of the key groove 65g, a restriction portion 655 is formed that is projected from the shaft 65d outwardly in the circumferential direction of the shaft 65d. The restriction portion 655 is formed in an annular shape as seen in the Y direction. As illustrated in FIG. 10, the movement of the first linkage member 651 in the Y direction is restricted by the restriction portion 655. Therefore, the first linkage member 651 more reliably rotates integrally with the shaft 65d.

As illustrated in FIGS. 10 and 11, the first linkage member 651 is provided on one side (Y1 side) in the axial direction of the shaft 65d and includes a first linkage projection 651b projected toward the other side (Y2 side) of the axial direction (Y direction) so as to be linked to the second linkage member 652 in such a manner that the first linkage member 651 can rotate with the second linkage member 652. The second linkage member 652 is arranged on the other side (Y2 side) in the axial direction (Y direction) and includes a second linkage projection 652a projected toward the one side (Y1 side) of the axial direction (Y direction) so as to be linked to the first linkage member 651 in such a manner that the second linkage member 652 can rotate with the first linkage member 651.

With this configuration, the first linkage member 651 and the second linkage member 652 are easily linked with each other to rotate together by means of the first linkage projection 651b of the first linkage member 651 and the second linkage projection 652a of the second linkage member 652.

As illustrated in FIG. 11, in the first linkage member 651, the first linkage projection 651b and the key 651a are arranged at positions opposite to each other in the circumferential direction of the annular first linkage member 651 (positions that differ by approximately 180 degrees).

Figure 13:
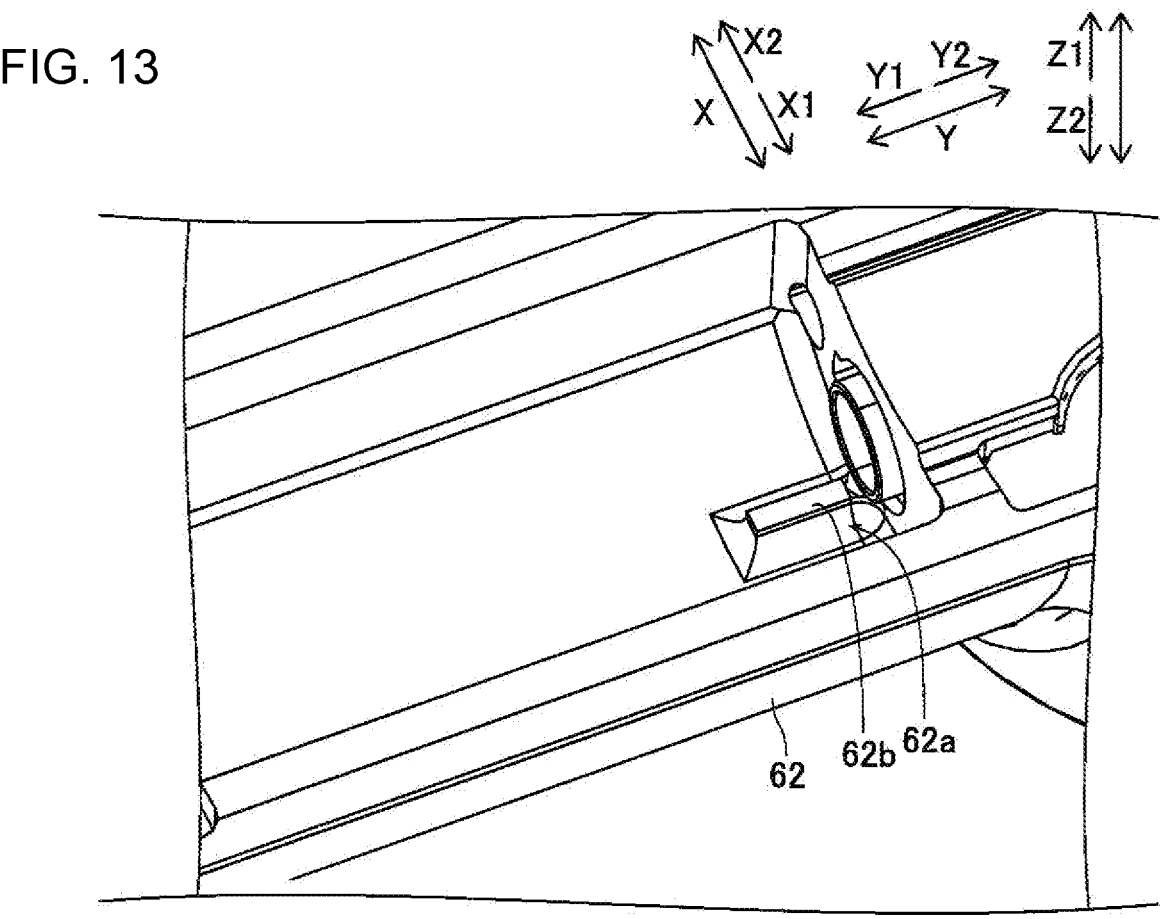
FIG. 13 is a diagram illustrating a perspective view of a stopper of the endoscope adaptor according to an embodiment.

As illustrated in FIG. 10, the second linkage member 652 includes a first stopper projection 652b that is projected outwardly in the radial direction of the shaft 65d to stop the rotation of the shaft 65d. As illustrated in FIG. 13, the stopper 62a includes a second stopper projection 62b that is projected toward the shaft 65d and configured to come in contact with the first stopper projection 652b of the second linkage member 652 when the second linkage member 652 rotates.

That is, the first stopper projection 652b of the second linkage member 652 comes in contact with the second stopper projection 62b of the stopper 62a, which causes the rotation of the second linkage member 652 to stop. As a result, the driven member 64 can be stopped at the mechanical end therefor.

As illustrated in FIG. 11, in the second linkage member 652, the second linkage projection 652a and the first stopper projection 652b are arranged at positions opposite to each other in the circumferential direction of the annular second linkage member 652 (positions that differ by approximately 180 degrees).

As illustrated in FIG. 10, on the Y2 side of the second linkage member 652, a restriction member 654 is provided to restrict the position of the second linkage member 652 in the Y direction. The restriction member 654 has an annular shape, as seen along the Y direction, formed with a through hole through which the shaft 65*d* passes. That is, the second linkage member 652 and third linkage members 653 (described later) are sandwiched between the first linkage member 651 and the restriction member 654 and thus the positions in the Y direction of the second linkage member 652 and the third linkage members 653 are restricted.

The transmission mechanism 65 further includes the third linkage members 653 provided between the first linkage member 651 and the second linkage member 652. As illustrated in FIG. 11, each of the third linkage members 653 includes: a third linkage projection 653*a* projected toward the one side (Y1 side) in the axial direction (Y direction) such that the third linkage member 653 is linkable with the first linkage member 651 and rotates together with the first linkage member 651 when being linked with the first linkage member 651; and a fourth linkage projection 653*b* projected toward the other side (the Y2 side) of the axial direction (Y direction) such that the third linkage member 653 is linkable with the second linkage member 652 and rotates together with the second linkage member 652 when being linked with the second linkage member 652.

Therefore, by means of the third linkage projection 653*a* of the third linkage member 653, the third linkage member 653 can be rotated together with the first linkage member 651. Further, by means of the fourth linkage projection 653*b*, the third linkage member 653 can be rotated together with the second linkage member 652. Since the third linkage members 653 are provided between the first linkage member 651 and the second linkage member 652 in such a manner that the third linkage members 653 come in linkage with the first linkage member 651 and the second linkage member 652 and thus are rotated together with the first linkage member 651 and the second linkage member 652, the rotation amount of the driven member 64 from the start of the rotation of the first linkage member 651 to the position where the second linkage member 652 comes in contact with the stopper 62*a* can be increased due to the provision of the third linkage members 653. As a result, the rotatable angle range of the driven member 64 can be increased.

The third linkage member 653 has an annular shape, as seen along the Y direction, formed with a through hole through which the shaft 65*d* passes. That is, the third linkage members 653 is formed in a ring shape like the first linkage member 651 and the second linkage member 652.

In the third linkage member 653, the third linkage projection 653*a* and the fourth linkage projection 653*b* are arranged at positions opposite to each other in the circumferential direction of the annular third linkage member 653 (positions that differ by approximately 180 degrees).

The plurality (two) of the third linkage members 653 are arranged side by side in the axial direction (Y direction). The plurality (two) of the third linkage members 653 are configured to be linkable with each other and rotate together when they are linked. Specifically, the fourth linkage projection 653*b* of the third linkage member 653 that is provided on the one side (Y1 side) in the axial direction (Y direction) comes in contact with (comes in engagement with) the third linkage projection 653*a* of the third linkage member 653 that is provided on the other side (Y2 side) in the axial direction (Y direction), and thus the two third linkage members 653 are linked with each other so the two third linkage members 653 can rotate together.

Accordingly, the rotation amount of the driven member 64 from the start of the rotation of the first linkage member 651 to the position where the second linkage member 652 comes in contact with the stopper 62*a* can be increased depending on the number of the third linkage members 653. As a result, the rotatable angle range of the driven member 64 can be easily increased. Further, in an embodiment, the shapes of the two of the third linkage members 653 are the same, and thus the manufacturing cost thereof is reduced.

Further, the driven member 64 is rotatable in the rotational angle range greater than 360 degrees. In other words, the drive part 201 (i.e., the engagement projection 201*a* of the drive part 201) is rotatable in the rotational angle range greater than 360 degrees.

Here, in a case where the rotatable angle range of the driven member 64 is greater than 360 degrees, the encoder 201*c* may be unable to recognize the rotational position of the engagement projection 201*a* of the drive part 201 since there may be a plurality of rotational positions, such as a certain position and a position rotated by 360 degrees from the certain position, in the same rotational direction of the driven member 64, which the encoder 201*c* cannot distinguish. In such a case, the endoscope adaptor 6 that is capable of positioning the endoscope 2*d* and the drive part 201 of the robot arm 2*a* to their home positions in the rotatable angle ranges thereof after the endoscope 2*d* is attached to the robot arm 2*a* can be effectively used.

Specifically, as illustrated in FIGS. 8A and 8B, the driven member 64 is rotatable from the home position (the state illustrated in FIG. 8A) to the positions (the mechanical ends) rotated by approximately 412 degrees in the clockwise direction and in the counterclockwise direction when viewed from the Z2 side. That is, the driven member 64 has the rotatable angle range of 824 degrees. In other words, since the drive part 201 (i.e., the engagement projection 201*a* of the drive part 201) is rotatable in the rotational angle range greater than 360 degrees (i.e., more than one rotation), the encoder 201*c* cannot distinguish between (i) a state where the drive part 201 is located at the home position of the drive part 201, (ii) a state where the drive part 201 is located at a position rotated by 360 degrees in the clockwise direction from the home position of the drive part 201, and (iii) a state where the drive part 201 is located at a position rotated by 360 degrees in the counterclockwise direction from the home position of the drive part 201. FIG. 8B illustrates a state where the driven member 64 is at a position (the mechanical end) where the driven member 64 is rotated by approximately 412 degrees in the counterclockwise direction as seen from the Z2 side.

The endoscope holder 61 is configured to hold the endoscope 2*d* to be rotatable in such a manner that the rotational position of the endoscope 2*d* and the rotational position of the driven member 64 have a constant relationship (are correlated with each other).

With this configuration, when the driven member 64 is positioned at the home position of the driven member 64, the endoscope 2*d* can be also positioned at a specific position (such as the home position of the endoscope 2*d*) in the rotational position of the endoscope. Therefore, after the endoscope 2*d* is attached to the robot arm 2*a*, by positioning the drive part 201 to the home position thereof, both of the endoscope 2*d* and the drive part 201 of the robot arm 2*a* can reliably be positioned at their home positions in the rotatable angle ranges thereof.

Specifically, as described above, the endoscope holder 61 holds the endoscope 2*d* in such a manner that the notch 67*d* of the endoscope holder 61 is engaged with the operation part 211 of the endoscope 2*d*. The endoscope holder 61 is configured such that the endoscope holder 61 is in the home position thereof when the notch 67*d* faces downward (the Z2 side). The endoscope holder 61 is configured to be rotatable from the home position thereof to positions rotated by 360 degrees in the clockwise direction and in the counterclockwise direction as viewed from the Y1 side. That is, approximately 412 degrees of the rotatable angle range of the driven member 64 corresponds to (is correlated with) approximately 360 degrees of the rotatable angle range of the endoscope 2d. In other words, approximately 412 degrees of the rotatable angle range of the drive part 201 (i.e., the engagement projection 201a) corresponds to (is correlated with) approximately 360 degrees of the rotatable angle range of the endoscope 2d.

As illustrated in FIG. 2, the robotic surgical system 100 according to an embodiment includes the robot arm 2a, the endoscope adaptor 6, and a controller 202. The controller 202 controls the drive parts 201 of the robot arm 2a. The controller 202 is configured to control to rotationally position the drive part 201 to the home position of the drive part 201 (i.e., the engagement projection 201a of the drive part 201), based on the rotational position of the drive part 201 (i.e., the engagement projection 201a of the drive part 201) of the robot arm 2a when the rotation of the shaft 65d is stopped, which is a reference point.

With this, by the control of the controller 202, the drive part 201 can be positioned to the home position of the drive part 201, based on the rotational position of the drive part 201 when the driven member 64 is located at the mechanical end of the driven member 64. That is, in the case where the home position of the drive part 201 is predetermined with respect to the rotatable angle range of the drive part 201 (i.e., the range between both of the mechanical ends of rotation of the drive part 201), the drive part 201 can be positioned to the predetermined home position by rotating the drive part 201 to move the drive part 201 (i.e., the engagement projection 201a of the drive part 201) from the mechanical end to the home position of the drive part 201 based on the relationship between the rotatable angle range of the drive part 201 and the predetermined home position of the drive part 201. Specifically, as described above, in an embodiment, the rotatable angle range of the drive part 201 (i.e., the engagement projection 201a of the drive part 201) is approximately 824 degrees with approximately 412 degrees in the counterclockwise direction (+412 degrees) and approximately 412 degrees in the clockwise direction (−412 degrees). Accordingly, by rotating the drive part 201 (i.e, the engagement projection 201a of the drive part 201) of the robot arm 2a by approximately 412 degrees from the state where the driven member 64 and the drive part 201 (i.e, the engagement projection 201a of the drive part 201) are located at the mechanical ends therefor, the driven member 64 and the drive part 201 (i.e, the engagement projection 201a of the drive part 201) are moved to their home positions (the rotational positions of 0 degrees). Further, by positioning the driven member 64 to the home position of the driven member 64, the endoscope 2d, which is held by the endoscope holder 61 to which the rotation of the driven member 64 is transmitted, can also be positioned to the home position of the endoscope 2d. As a result, it is possible to provide the robotic surgical system 100 that is capable of adjusting the rotational positions of the endoscope 2d and the drive part 201 of the robot arm 2a to the home positions thereof, after the endoscope 2d is attached to the robot arm 2a.

(Method of Adjusting Rotational Position Using Endoscope Adaptor)

Figure 14:
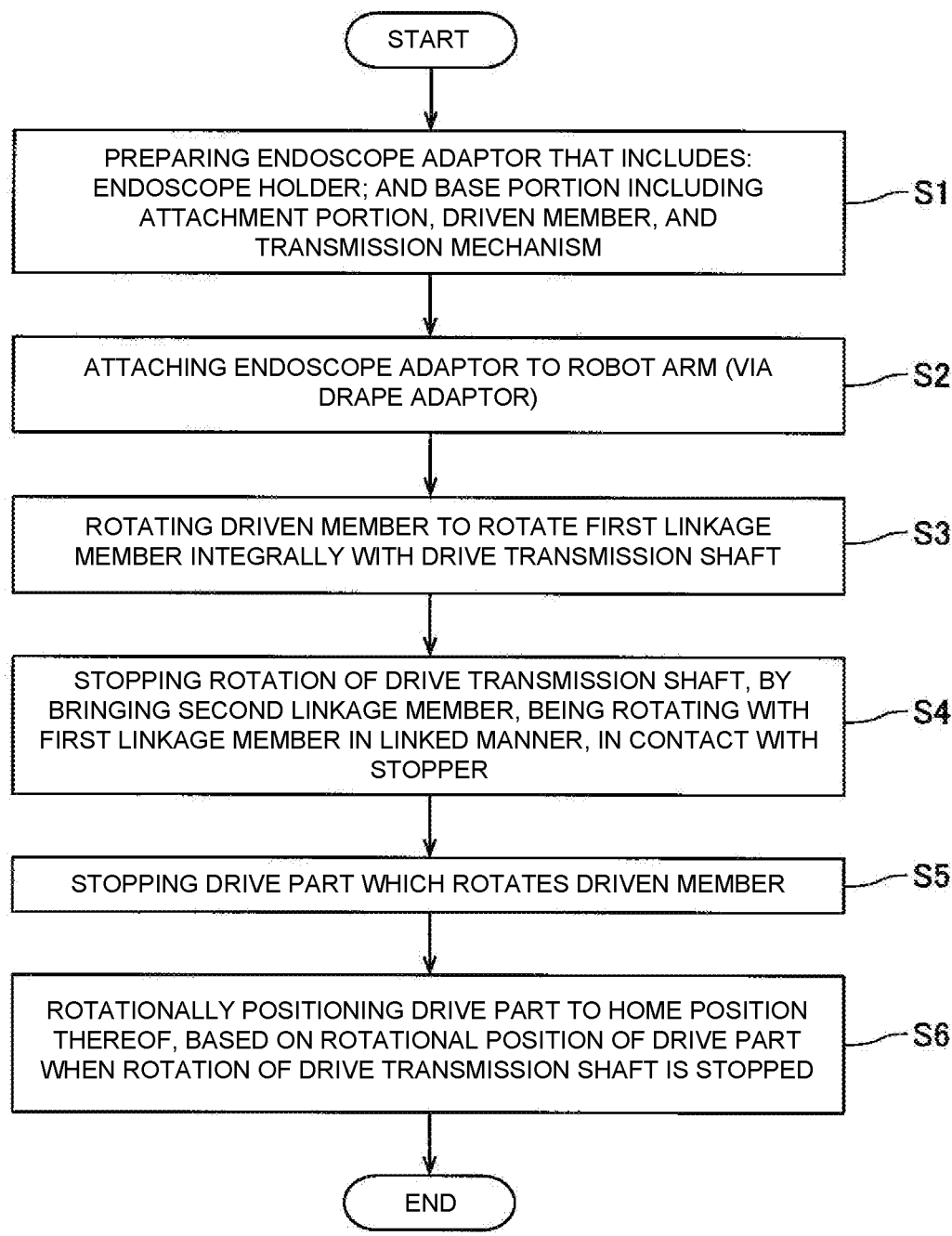
FIG. 14 is a flowchart of a method of adjusting rotational positions using the endoscope adaptor according to an embodiment.

With reference to FIG. 14, a method of adjusting the rotational position using the endoscope adaptor 6 according to an embodiment is described.

As illustrated in FIG. 14, the method of adjusting the rotational position using the endoscope adaptor 6 includes: a step (S1) of preparing the endoscope adaptor 6; a step (S3) of rotating the first linkage member 651 integrally with the shaft 65d; a step (S4) of stopping the rotation of the shaft 65d; and a step (S6) of rotationally positioning the drive part 201 (i.e., the engagement projection 201a of the drive part 201) to the home position thereof. The step (S1) of preparing the endoscope adaptor 6 is the step of preparing the endoscope adaptor 6 that includes the endoscope holder 61 that is configured to rotatably hold the endoscope 2d and the base portion 62, wherein the base portion 62 includes: the attachment portion 63 to be attached to (the drive part 201 of) the robot arm 2a (via the drape adaptor 7); the driven member 64 that is provided in the attachment portion 63 and is to be driven to rotate by the drive part 201 of the robot arm 2a (via the drape adaptor 7); and the transmission mechanism 65 that is configured to decelerate and transmit the rotation of the driven member 64 to the endoscope holder 61. The step (S3) of rotating the first linkage member 651 integrally with the shaft 65d is the step of, in the state where the endoscope adaptor 6 is attached to the robot arm 2a, rotating the driven member 64 to rotate the shaft 65d by the rotation of the driven member 64 so as to rotate the first linkage member 651 integrally with the shaft 65d. The step (S4) of stopping the rotation of the shaft 65d is the step of stopping the rotation of the shaft 65d by bringing the first stopper projection 652b of the second linkage member 652 that is being integrally rotated with the first linkage member 65 via the third linkage members 653, in contact with the stopper 62a of the base portion 62. The step (S6) of rotationally positioning the drive part 201 (i.e., the engagement projection 201a of the drive part 201) to the home position of the drive part 201 is the step of, after the step (S4) of stopping the rotation of the shaft 65d, rotationally positioning the drive part 201 (i.e., the engagement projection 201a of the drive part 201) to the home position of the drive part 201, based on the rotational position of the drive part 201 (i.e., the engagement projection 201a of the drive part 201) of the robot arm 2a when the rotation of the shaft 65d is stopped, which is the reference point.

In the method of adjusting the rotational position using the endoscope adaptor 6 according to an embodiment, after the endoscope adaptor 6 is attached to the robot arm 2a, the driven member 64 is rotated (by the drive part 201) to rotate the first linkage member 651 integrally with the shaft 65d and then to link the first linkage member 651 to the second linkage member 652 so as to rotate the first linkage member 651 together with the first linkage member 651, and then the rotation of the shaft 65d is stopped when the first stopper projection 652b of the second linkage member 652 comes in contact with the second stopper projection 62b of the stopper 62a. With this operation, the rotational position of the driven member 64 is located at the mechanical end (the mechanical movement limit) for the driven member 64. Further, in the method of adjusting the rotational position using the endoscope adaptor 6 according to an embodiment, after the rotation of the shaft 65d is stopped, the drive part 201 is rotationally positioned to the home position of the drive part 201, based on the rotational position of the drive part 201 (i.e., the engagement projection 201a of the drive part 201) of the robot arm 2a when the rotation of the shaft 65d is stopped. With this, the drive part 201 can be positioned to the home position of the drive part 201, based on the rotational position of the drive part 201 (i.e., the engagement projection 201a of the drive part 201) when the driven member 64 is located at the mechanical end for the driven member 64. That is, by rotating the drive part 201 to move the driven member 64 from the mechanical end to the home position of the driven member 64, the drive part 201 is positioned to the home position of the drive part 201 and the endoscope 2d, which is held by the endoscope holder 61 to which the rotation of the driven member 64 is transmitted, is also positioned to the home position of the endoscope 2d. As a result, it is possible to position the endoscope 2d and the drive part 201 of the robot arm 2a to the home positions in the rotatable angle ranges thereof, after the endoscope 2d is attached to the robot arm 2a.

Specifically, in step S1, the step is performed of preparing the endoscope adaptor 6 including the endoscope holder 61 and the base portion 62, wherein the base portion 62 includes the attachment portion 63, the driven member 64, and the transmission mechanism 65.

Next, in step S2, a step is performed of attaching the endoscope adaptor 6 to the robot arm 2a via the drape adaptor 7. Here, when the endoscope adaptor 6 is attached to the drive part 201 of the robot arm 2a via the drape adaptor 7, the position (the rotational position) of the driven member 64 in the rotatable angle range of the driven member 64 is unknown (random). Therefore, the position (the rotational position) of the engagement projection 201a of the drive part 201 of the robot arm 2a also is unknown (random). Thus, it is necessary to position the endoscope 2d and the drive part 201 of the robot arm 2a to the home positions in the rotatable angle ranges thereof.

Next, in step S3, the step is performed of rotating the driven member 64 to rotate the first linkage member 651 integrally with the shaft 65d. Specifically, by the drive part 201 of the robot arm 2a, the driven member 64 is driven to rotate and the rotation of the driven member 64 is accelerated to rotate the shaft 65d. With this, the first linkage member 651 fixed to the shaft 65d is rotated integrally with the shaft 65d.

Next, in step S4, the step is performed of stopping the rotation of the shaft 65d, by bringing the second linkage member 652, which is linked to and rotating together with the first linkage member 651 via the third linkage members 653, in contact with the stopper 62a.

Specifically, by the rotation of the first linkage member 651 integrally with the shaft 65d, the first linkage projection 651b of the first linkage member 651 comes in contact with the third linkage projection 653a of the third linkage member 653 on the Y1 side, so that the third linkage member 653 on the Y1 side starts to rotate together with the first linkage member 651. Then, the fourth linkage projection 653b of the third linkage members 653 on the Y1 side comes in contact with the third linkage projection 653a of the third linkage members 653 on the Y2 side, so that the third linkage member 653 on the Y2 side starts to rotate together with the third linkage member 653 on the Y1 side and the first linkage member 651. Then, the fourth linkage projection 653b of the third linkage members 653 on the Y2 side comes in contact with the second linkage projection 652a of the second linkage member 652, so that the second linkage member 652 starts to rotate together with the first linkage member 651 via the third linkage member 653 on the Y1 side and the third linkage member 653 on the Y2 side. Then, the first stopper projection 652b of the second linkage member 652 comes in contact with the second stopper projection 62b of the stopper 62a. With this, the rotations of the first linkage member 651, the third linkage member 653 on the Y1 side, the third linkage member 653 on the Y2 side, and the second linkage member 652, which have been rotated together, are hindered and thus stopped.

Note that in step S4, the controller 202 controls to rotate the drive part 201 (i.e., the engagement projection 201a of the drive part 201) at a predetermined rotational speed. That is, in step S4, the driven member 64 is rotated at a predetermined rotational speed. Then, when the rotational position of the driven member 64 approaches the same position as the mechanical end (a position rotated approximately 52 degrees (+52 degrees) in the counterclockwise direction, a position rotated approximately 52 degrees (−52 degrees) in the clockwise direction), the controller 202 decreases the rotational speed of the driven member 64 once. Then, if the rotation of the driven member 64 does not stop (if the rotational position of the driven member 64 is not the mechanical end), the controller 202 increases the rotation speed of the driven member 64 back to the predetermined rotation speed, and continues to rotate the driven member 64. The rotational position of the driven member 64 is detected, for example, indirectly by detecting the rotational position of the motor 201b of the drive part 201 by the encoder 201c of the drive part 201.

Next, the step (S5) is performed of stopping the drive part 201 that has been rotating the driven member 64.

That is, the method of adjusting the rotational position using the endoscope adaptor 6 includes the step (S5) of stopping the drive part 201 that has been rotating the driven member 64, after the step (S4) of stopping the rotation of the shaft 65d and before the step (S6) of positioning the drive part 201 to the home position of the drive part 201. The drive part 201 includes the motor 201b. The step (S5) of stopping the drive part 201 is the step of stopping the drive part 201 based on the output current value of the motor 201b.

If the driving of the motor 201b is continued after the second linkage member 652 comes in contact with the stopper 62a and the rotation of the shaft 65d is stopped, the output current value of the motor 201b rises sharply. Therefore, it is easily determined, based on the output current value of the motor 201b, that the rotation of the shaft 65d is stopped as the second linkage member 652 comes in contact with the stopper 62a.

Further, the step (S5) of stopping the drive part 201 is the step of stopping the drive part 201 based on the rotational position of the motor 201b in addition to the output current value of the motor 201b.

Therefore, it is more accurately determined that the rotation of the shaft 65d is stopped as the second linkage member 652 comes in contact with the stopper 62a, than a case of determining only based on the output current value of the motor 201b.

Note that the rotational position of the motor 201b is detected by the encoder 201c of the drive part 201. Thus, it is easily determined, based on the fact that the rotational position of the motor 201b does not change, that the rotation of the shaft 65d is stopped as the second linkage member 652 comes in contact with the stopper 62a.

Next, in step S6, the step is performed of rotationally positioning the drive part 201 to the home position of the drive part 201, based on the rotational position of the drive part 201 when the rotation of the shaft 65d is stopped.

The step (S6) of positioning the drive part 201 to the home position of the drive part 201 is the step of positioning the drive part 201 to the home position of the drive part 201 by rotating the drive part 201 by the predetermined angle in the reverse direction.

Accordingly, in the step (S6) of positioning the drive part 201 to the home position thereof, the drive part 201 is easily moved to the home position of the drive part 201 somewhere in the rotatable angle range of the drive part 201, by rotating the drive part 201 from the mechanical end of the drive part 201 in the direction (the reverse direction) opposite to the rotational direction of the drive part 201 in the step (S3) of rotating the first linkage member 651 integrally with the shaft 65d and in the step (S4) of stopping the rotation of the shaft 65d.

Specifically, in the state where the rotational position of the driven member 64 is located at the mechanical end thereof, the drive part 201 rotates the driven member 64, by the predetermined angle (approximately 412 degrees) from the mechanical end to the home position, in the rotational direction (the reverse direction) opposite to the rotational direction in the step (S4) of stopping the shaft 65d. With this, the rotational position of the driven member 64 is set to the home position of the driven member 64. Then, the controller 202 sets the rotational position of the drive part 201 of the robot arm 2a in the state where the rotational position of the driven member 64 is located at the home position of the driven member 64 as the home position of the drive part 201. With this, the endoscope 2d and the drive part 201 of the robot arm 2a can be located (initialized) to the home positions in the rotatable angle ranges thereof.

(Modifications)

It should be understood that one or more embodiments described above are illustrated by way of example in every respect and not limit the disclosure. The scope of the invention is indicated by claims, not by explanation of the one or more embodiments described above, and includes equivalents to the claims and all alterations (modifications) within the same.

For example, in one or more embodiments described above, the step (S5) of stopping the drive part 201 is performed based on the rotational position of the motor 201b in addition to the output current value of the motor 201b. However, the disclosure is not limited thereto. In the disclosure, the step of stopping the drive part may be performed to stop the drive part based only on the output current value of the motor. Also, in the disclosure, the step of stopping the drive part may be performed to stop the drive part based only on the rotational position of the motor.

In one or more embodiments described above, the case has been described in which the driven member 64 is configured to be rotatable within the rotatable angle range greater than 360 degrees, but the disclosure is not limited thereto. In the disclosure, the driven member may be rotatable in the rotational angle range smaller than 360 degrees.

In one or more embodiments described above, the plural (two) third linkage members 653 are arranged in the axial direction (Y direction) side by side between the first linkage member 651 and the second linkage member 652 in the axial direction (Y direction), wherein each of the third linkage members 653 includes the third linkage projection 653a to be linked to the first linkage member 651 so as to be rotated along with the first linkage member 651 and the fourth linkage projection 653b to be linked to the second linkage member 652 so as to be rotated along with the second linkage member 652. However, the disclosure is not limited to this. In the disclosure, only a single third linkage member or three or more third linkage members may be provided side by side in the axial direction between the first linkage member and the second linkage member, wherein the third linkage member includes the third linkage projection to be linkable to the first linkage member such that the third linkage member rotates together with the first linkage member when being linked to the first linkage member and the fourth linkage projection to be linkable to the second linkage member such that the third linkage member rotates together with the second linkage member when being linked to the second linkage member.

In one or more embodiments described above, the transmission mechanism 65 includes the third linkage members 653 between the first linkage member 651 and the second linkage member 652 in the axial direction (Y direction), wherein each of the third linkage members 653 includes the third linkage projection 653a to be linked with the first linkage member 651 so as to be rotated along with the first linkage member 651 and the fourth linkage projection 653b to be linked with the second linkage member so as to be rotated along with the second linkage member 652. However, the disclosure is not limited to this. In the disclosure, the transmission member may include no third linkage member.

In one or more embodiments described above, the case has been described in which the second linkage member 652 is configured to include the first stopper projection 652b projected outwardly in the radial direction of the shaft 65d to stop the rotation of the shaft 65d and the stopper 62a is configured to include the second stopper projection 62b projected toward the shaft 65d to come in contact with the first stopper projection 652b of the second linkage member 652 when the second linkage member 652 is rotated. However, the disclosure is not limited thereto. In the disclosure, the second linkage member may be configured to include a first stopper projection projected toward one side along the axial direction of the drive transmission shaft to stop the rotation of the drive transmission shaft. In such a case, a projection amount of the second stopper projection of the stopper toward the drive transmission shaft may be larger than the case where the first stopper projection of the second linkage member is projected outwardly in the radial direction of the drive transmission shaft so as to bring the first stopper projection of the second linkage member in contact with the second stopper projection of the stopper.

In one or more embodiments described above, the case has been described in which the first linkage projection 651b and the key 651a of the first linkage member 651 are provided at the positions opposite to each other in the circumferential direction of the annular first linkage member 651 (the positions that differ by approximately 180 degrees). However, the disclosure is not limited to this. In the disclosure, the first linkage projection and the key of the first linkage member may not be provided at the positions opposite to each other in the circumferential direction of the annular first linkage member as seen along the Y direction. Likewise, in one or more embodiments described above, the case has been described in which the second linkage projection 652a and the first stopper projection 652b of the second linkage member 652 are provided at the positions opposite to each other in the circumferential direction of the annular second linkage member 652 (the positions that differ by approximately 180 degrees). However, the disclosure is not limited to this. In the disclosure, the second linkage projection and the first stopper projection of the second linkage member may not be provided at the positions opposite to each other in the circumferential direction of the annular second linkage member as seen along the Y direction. Likewise, in one or more embodiments described above, the case has been described in which the third linkage projection 653a and the fourth linkage projection 653b of the third linkage member 653 are provided at the positions opposite to each other in the circumferential direction of the annular third linkage member 653 (the positions that differ by approximately 180 degrees). However, the disclosure is not limited to this. In the disclosure, the third linkage projection and the fourth linkage projection of the third linkage member may not be provided at the positions opposite to each other in the circumferential direction of the annular third linkage member as seen along the Y direction.

In one or more embodiments described above, the case has been described in which the rotational positions of the endoscope and the drive part of the robot arm are moved to the home positions thereof, when (just after) the endoscope is attached to the robot arm. However, the disclosure is not limited thereto. In the disclosure, the step of rotationally positioning the endoscope and the drive part of the robot arm to the home positions thereof may be performed at a time other than the time when (just after) the endoscope is attached to the robot arm (for example, at a time when an operator wants to reposition (reinitialize) the endoscope and the drive part of the robot arm to the home positions thereof after the endoscope is attached to the robot arm).

The invention claimed is:

1. An endoscope adaptor comprising:
    an endoscope holder; and
    a base rotatably supporting the endoscope holder, the base being provided with:
        a disk rotatably provided in the base and including a projection or a recess configured to be engaged directly or indirectly with a drive part of a robot arm; and
        a transmission mechanism configured to decelerate and transmit rotation of the disk to the endoscope holder, wherein
    the transmission mechanism comprises:
    a drive transmission shaft configured to be rotated by the rotation of the disk;
    a first cylinder formed with a through hole through which the drive transmission shaft passes and engaged with the drive transmission shaft to rotate integrally with the drive transmission shaft; and
    a second cylinder formed with a through hole through which the drive transmission shaft passes and rotatable with respect to the drive transmission shaft and configured to be linked to the first cylinder so as to rotate with the first cylinder when the first cylinder and the second cylinder are linked to each other, and
    the base includes a stopper projection provided at a position to come in contact with the second cylinder to stop rotation of the drive transmission shaft.

2. The endoscope adaptor according to claim 1, wherein the disk is rotatable in a rotational angle range greater than 360 degrees.

3. The endoscope adaptor according to claim 1, wherein the second cylinder includes a first stopper projection projected outwardly from the second cylinder in a radial direction of the drive transmission shaft to stop the rotation of the drive transmission shaft, and
    the stopper projection includes a second stopper projection projected toward the drive transmission shaft and provided at a position to come in contact with the first stopper projection of the second cylinder when the second cylinder rotates.

4. The endoscope adaptor according to claim 1, wherein the second cylinder includes a first stopper projection projected from the second cylinder toward one side along an axial direction of the drive transmission shaft to stop the rotation of the drive transmission shaft, and
    the stopper projection includes a second stopper projection projected toward the drive transmission shaft and provided at a position to come in contact with the first stopper projection of the second cylinder when the second cylinder rotates.

5. The endoscope adaptor according to claim 1, wherein the drive transmission shaft includes a key groove, and
    the first cylinder includes a key being engaged with the key groove.

6. The endoscope adaptor according to claim 1, wherein the first cylinder is provided on one side in an axial direction of the drive transmission shaft with respect to the second cylinder and includes a first cylinder projection projected toward the other side in the axial direction and configured to be linked to the second cylinder such that the first cylinder rotates together with the second cylinder, and
    the second cylinder includes a second cylinder projection projected toward the one side in the axial direction and configured to be linked to the first cylinder such that the second cylinder rotates together with the first cylinder.

7. The endoscope adaptor according to claim 6, wherein the transmission mechanism further comprises a third cylinder provided between the first cylinder and the second cylinder in the axial direction, wherein the third cylinder includes a third cylinder projection projected toward the one side along the axial direction and configured to be linked with the first cylinder such that the third cylinder rotates together with the first cylinder and a fourth cylinder projection projected toward the other side along the axial direction and configured to be linked with the second cylinder such that the third cylinder rotates together with the second cylinder.

8. The endoscope adaptor according to claim 7, wherein the third cylinder projection and the fourth cylinder projection are provided at positions opposite to each other in a circumferential direction of the third cylinder as seen along the axial direction.

9. The endoscope adaptor according to claim 7, wherein the third cylinder comprises a plurality of third cylinders arranged in the axial direction, and
    the plurality of third cylinders are linkable with each other to rotate together when the plurality of third linkages are linked with each other.

10. The endoscope adaptor according to claim 9, wherein the plurality of third cylinders have a same shape.

11. The endoscope adaptor according to claim 1, wherein the endoscope holder is configured to hold an endoscope to be rotatable in such a manner that a rotational position of the endoscope and a rotational position of the disk are correlated with each other.

12. The endoscope adaptor according to claim 11, wherein the endoscope holder includes a notch configured to be engaged with the endoscope, and
    the notch is configured to position the endoscope with respect to the endoscope holder.

13. The endoscope adaptor according to claim 1, wherein the base is configured to be attached to the drive part of the robot arm via a drape adaptor that holds a drape.

14. A robotic surgical system, comprising:
    a robot arm;
    an endoscope adaptor connected to the robot arm; and
    a controller configured to control a drive part of the robot arm, wherein
    the endoscope adaptor comprises:
    an endoscope holder;
    a base rotatably supporting the endoscope holder, the base being provided with:

a disk rotatably provided in the base and including a projection or a recess configured to be engaged directly or indirectly with the drive part of the robot arm so as to be rotated by the drive part of the robot arm; and a transmission mechanism configured to decelerate and transmit rotation of the disk to the endoscope holder, wherein the transmission mechanism comprises:
- a drive transmission shaft configured to be rotated by the rotation of the disk;
- a first cylinder formed with a through hole through which the drive transmission shaft passes and engaged with the drive transmission shaft to rotate integrally with the drive transmission shaft; and
- a second cylinder formed with a through hole through which the drive transmission shaft passes and rotatable with respect to the drive transmission shaft and configured to be linked to the first cylinder so as to rotate along with the first cylinder when the first cylinder and the second cylinder are engaged with eath other, the base includes a stopper projection provided at a position to come in contact with the second cylinder to stop rotation of the drive transmission shaft, and the controller is configured to rotationally position the drive part to a home position of the drive part, based on a rotational position of the drive part of the robot arm when the second cylinder comes in contact with the stopper projection and thus the rotation of the drive transmission shaft is stopped.

15. The robotic surgical system according to claim 14, wherein the drive part includes a motor and an encoder that detects a rotational position of the motor, and the controller is configured:
(i) to rotate the motor in a first rotational direction until the second cylinder comes in contact with the stopper projection; and
(ii) to rotate the motor in a second rotational direction opposite to the first rotational direction by a predetermined angle from the rotational position of the drive part when the second cylinder comes in contact with the stopper projection and thus the rotation of the drive transmission shaft is stopped, so as to rotationally position the drive part to the home position of the drive part.

16. The robotic surgical system according to claim 15, wherein the predetermined angle is greater than 360 degrees.

* * * * *